US008992866B2

(12) United States Patent
Gelbman et al.

(10) Patent No.: US 8,992,866 B2
(45) Date of Patent: Mar. 31, 2015

(54) AUTOMATED, REFRIGERATED SPECIMEN INVENTORY MANAGEMENT SYSTEM

(75) Inventors: Alexander Gelbman, Florham Park, NJ (US); Mark Edwards, Armonk, NY (US); Matthew Rosmarin, Flushing, NY (US); Ilya Malyarov, Livingston, NJ (US); Benjamin Pollack, Budd Lake, NJ (US); Elizabeth Bononno, Long Valley, NJ (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 343 days.

(21) Appl. No.: 13/511,885

(22) PCT Filed: Nov. 23, 2010

(86) PCT No.: PCT/US2010/057771
§ 371 (c)(1),
(2), (4) Date: May 24, 2012

(87) PCT Pub. No.: WO2011/066269
PCT Pub. Date: Jun. 3, 2011

(65) Prior Publication Data
US 2012/0283867 A1 Nov. 8, 2012

Related U.S. Application Data

(60) Provisional application No. 61/263,842, filed on Nov. 24, 2009.

(51) Int. Cl.
*B65G 1/02* (2006.01)
*B01L 7/00* (2006.01)
(Continued)

(52) U.S. Cl.
CPC . *G01N 35/04* (2013.01); *B01L 7/02* (2013.01); *G01N 2035/00435* (2013.01); *G01N 2035/0425* (2013.01)
USPC ............... 422/565; 422/566; 422/63; 62/378; 414/267

(58) Field of Classification Search
None
See application file for complete search history.

(56) References Cited

U.S. PATENT DOCUMENTS 2,393,238 A * 1/1946 Dailey ............................ 62/258
4,963,493 A * 10/1990 Daftsios ........................ 422/566
(Continued)

FOREIGN PATENT DOCUMENTS

JP 62-001553 A 1/1987
JP 62-245156 A 10/1987
(Continued)

OTHER PUBLICATIONS

English translation of Japanese Office Action dated Jan. 28, 2014 of corresponding Japanese Patent Application No. 2012-541158, 10 Pages.

*Primary Examiner* — Jill Warden
*Assistant Examiner* — Benjamin Whatley
(74) *Attorney, Agent, or Firm* — PretiFlaherty, LLP

(57) ABSTRACT

An automated, refrigerated specimen management system (ARSIMS) to hold sealed and/or opened sample/specimen tubes and/or containers that can be in the pre-analytical, in-process, or post-analytical phase of processing. The ARSIMS ensures that each sample/specimen tube, whether it is sealed, capped, closed or open, can be stored at an ideal storage temperature according to the particular phase of processing and as appropriate for the combination of sample/specimen type and analyte(s) to be tested.

29 Claims, 36 Drawing Sheets

(51) Int. Cl.
*G01N 35/04* (2006.01)
*B01L 7/02* (2006.01)
*G01N 35/00* (2006.01)

(56) References Cited

U.S. PATENT DOCUMENTS

| | | | |
|---|---|---|---|
| 6,625,991 B1 * | 9/2003 | Clark | 62/3.6 |
| 2003/0156996 A1 * | 8/2003 | Delorme | 422/102 |
| 2004/0256963 A1 * | 12/2004 | Affleck et al. | 312/209 |
| 2005/0241333 A1 | 11/2005 | Hamilton | |
| 2007/0105214 A1 * | 5/2007 | Micklash et al. | 435/306.1 |
| 2007/0172396 A1 * | 7/2007 | Neeper et al. | 422/104 |
| 2008/0176209 A1 | 7/2008 | Muller et al. | |
| 2008/0260511 A1 * | 10/2008 | Fattinger et al. | 414/788.1 |
| 2008/0272674 A1 * | 11/2008 | Malin | 312/209 |
| 2012/0272500 A1 * | 11/2012 | Reuteler | 29/428 |
| 2013/0011226 A1 * | 1/2013 | Camenisch et al. | 414/277 |
| 2014/0127818 A1 * | 5/2014 | Fritchie et al. | 436/43 |

FOREIGN PATENT DOCUMENTS

| | | |
|---|---|---|
| JP | Hei 02-025331 A | 1/1990 |
| JP | Hei 05-076366 A | 3/1993 |
| JP | 2001-074750 A | 3/2001 |
| JP | 2006-282332 A | 10/2006 |
| JP | 2007-506944 A | 3/2007 |
| JP | 2009-204409 A | 9/2009 |

* cited by examiner

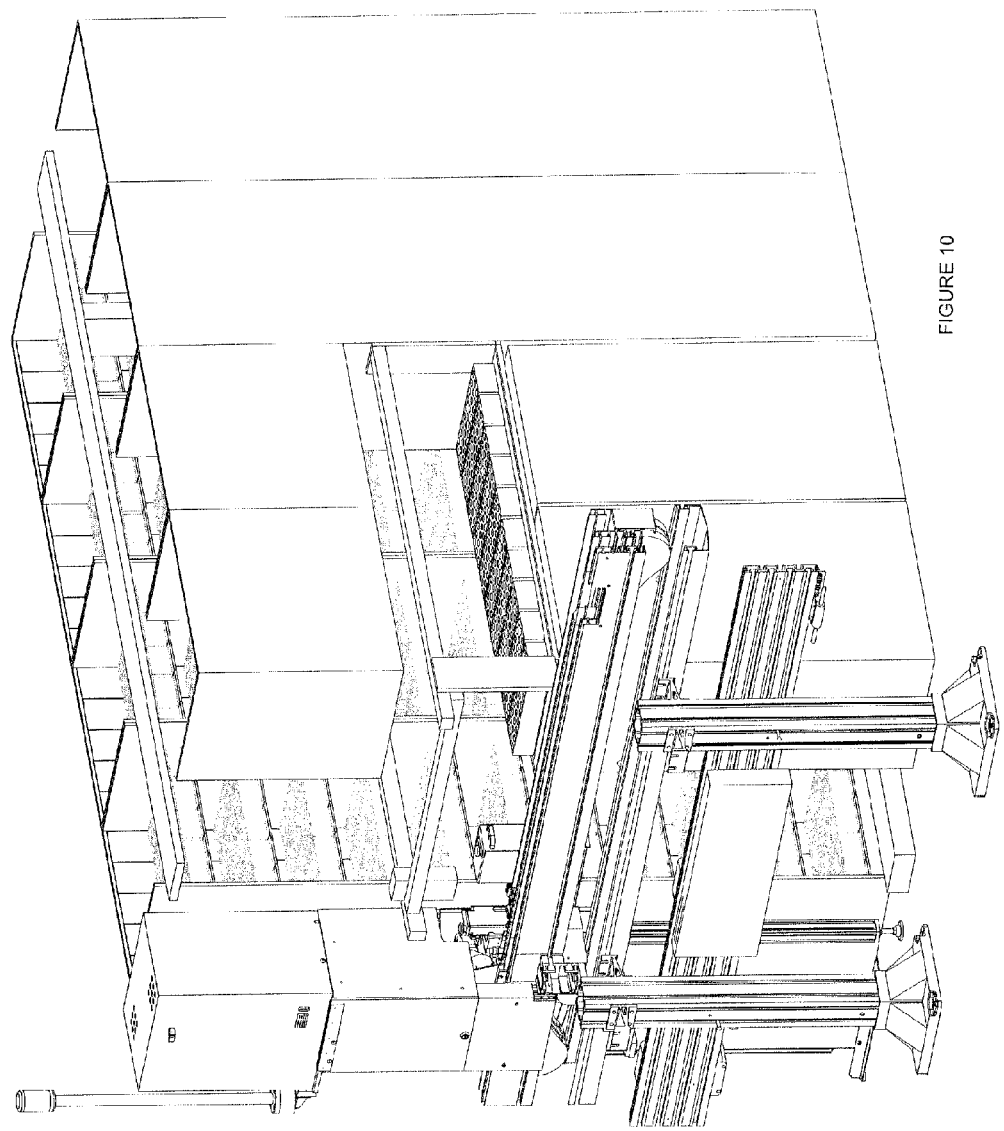

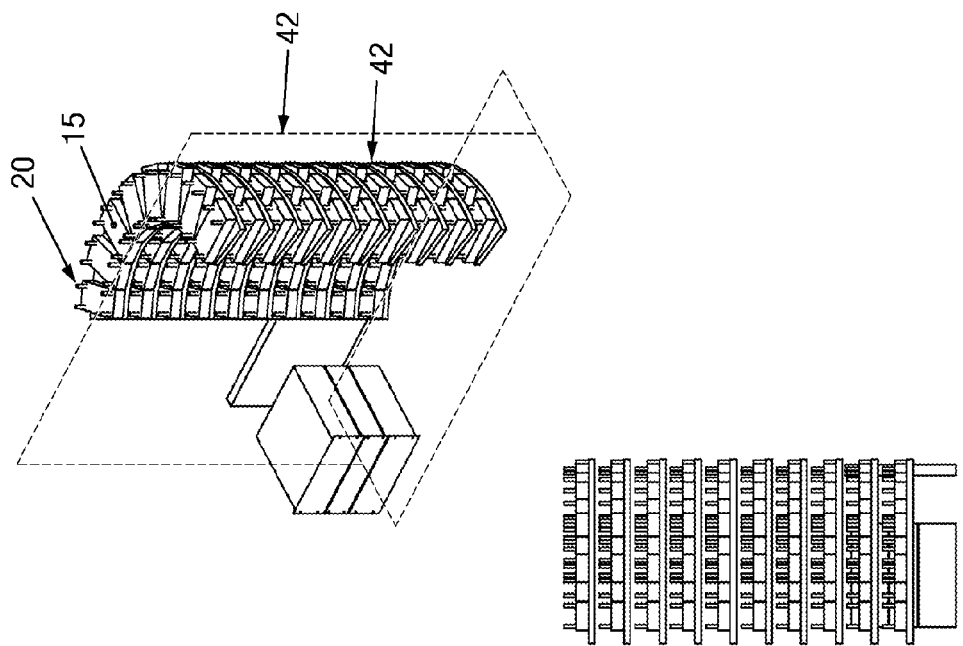
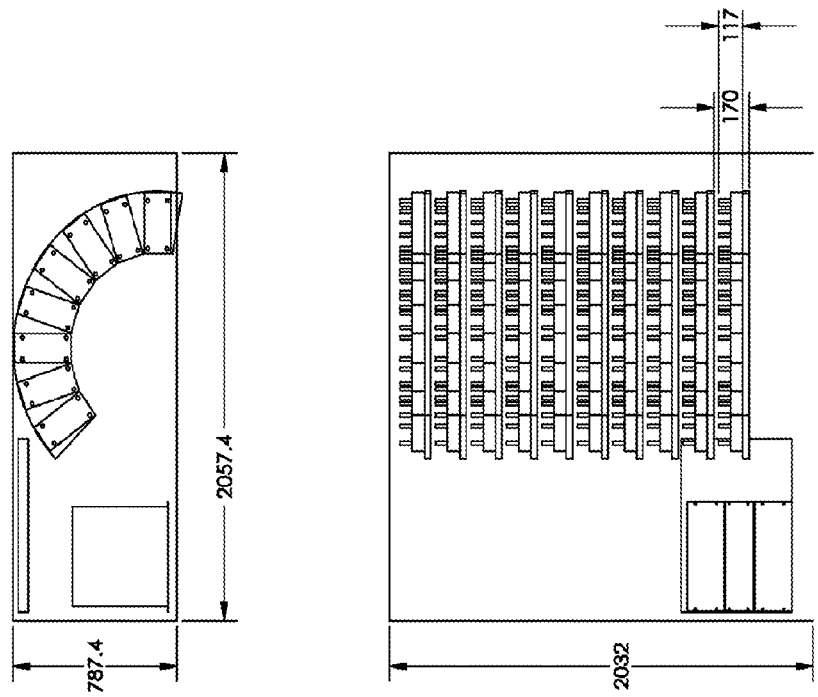
FIGURE 12A

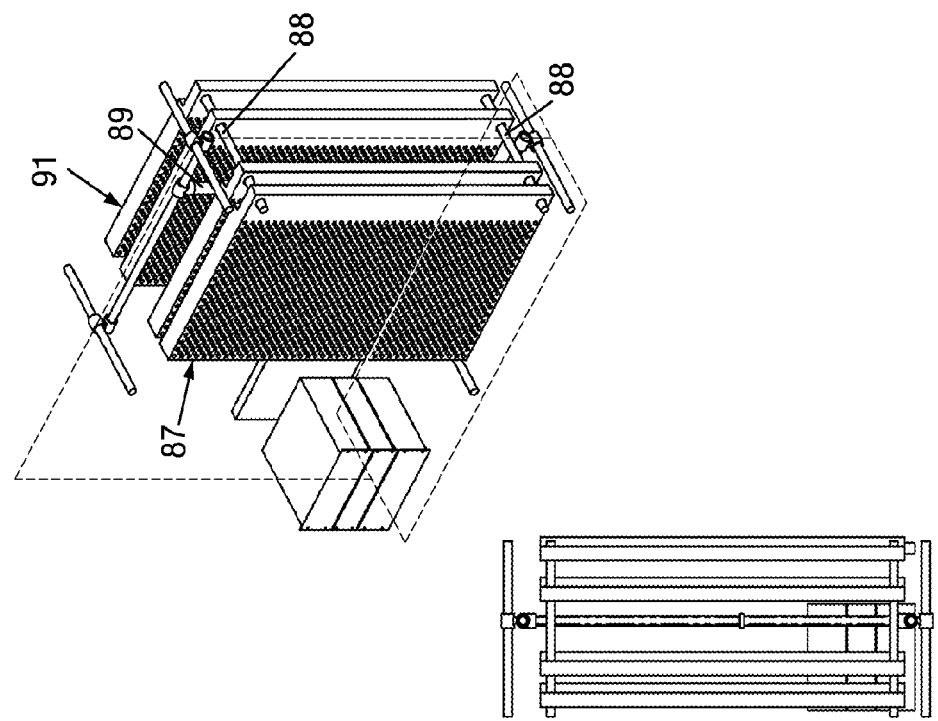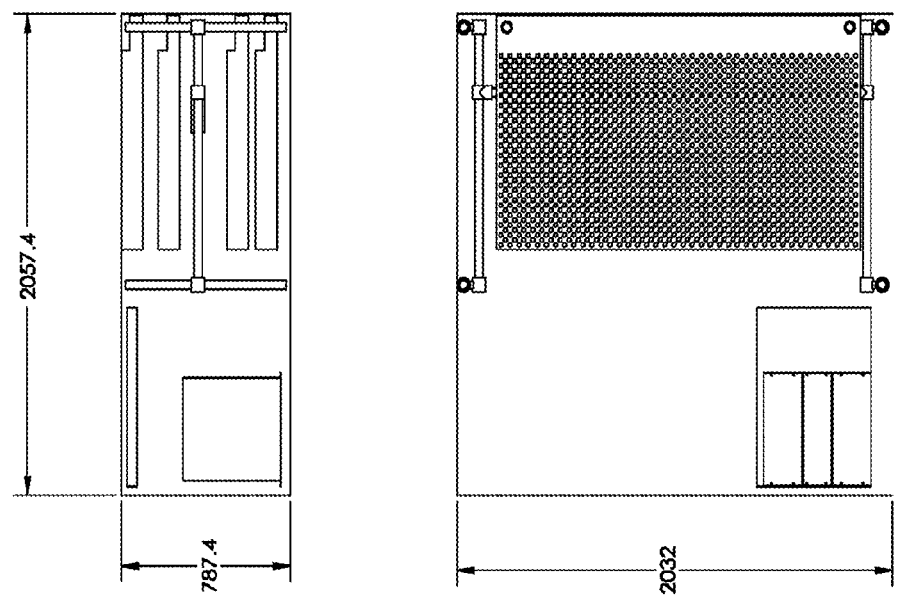
FIGURE 12B

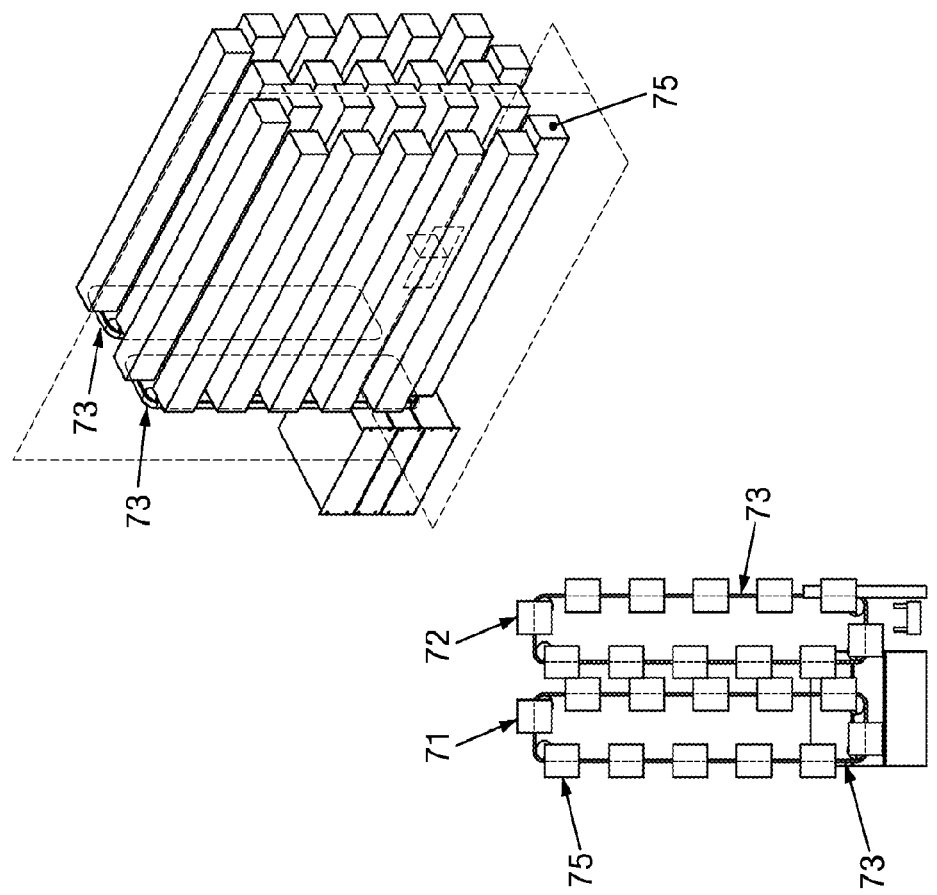
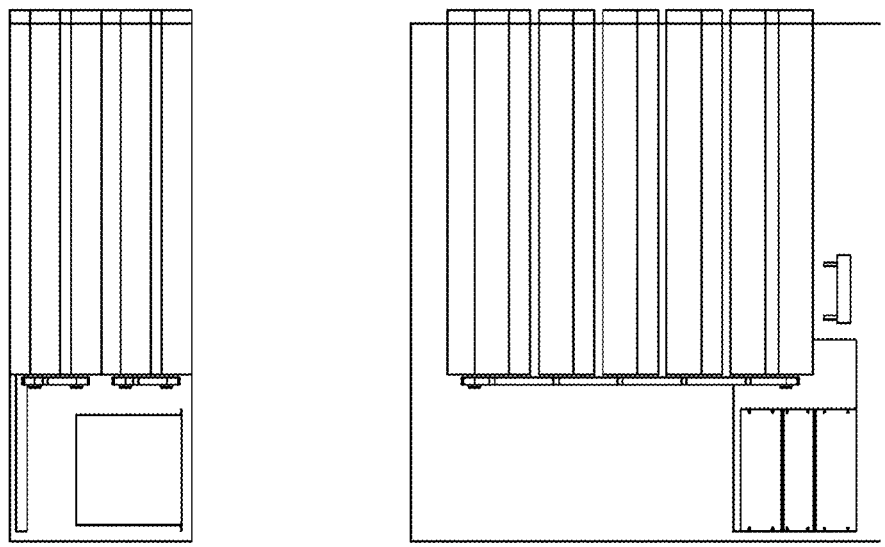
FIGURE 12C

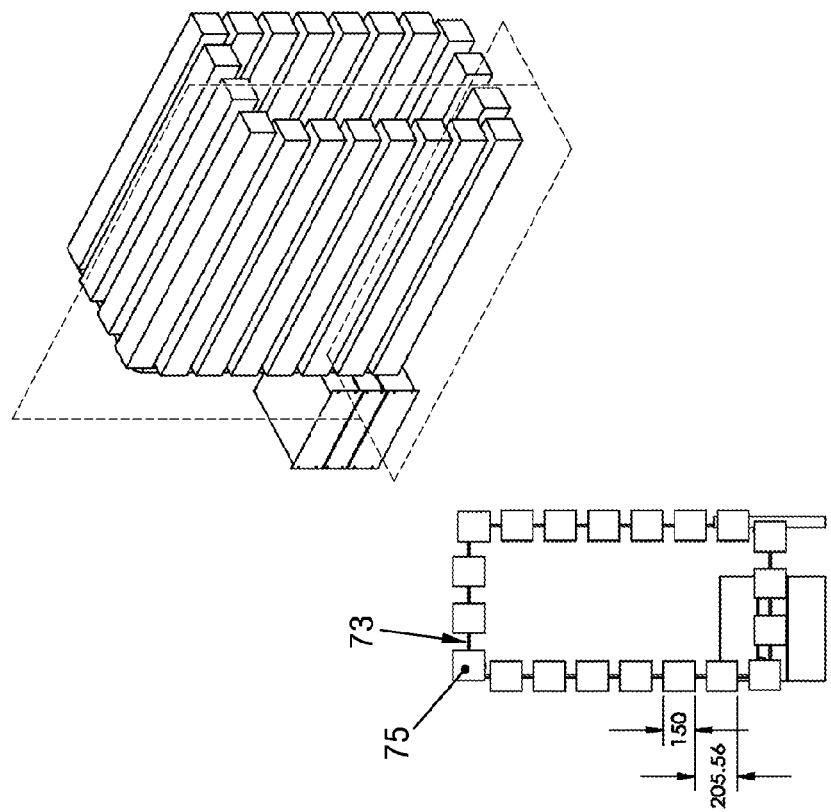
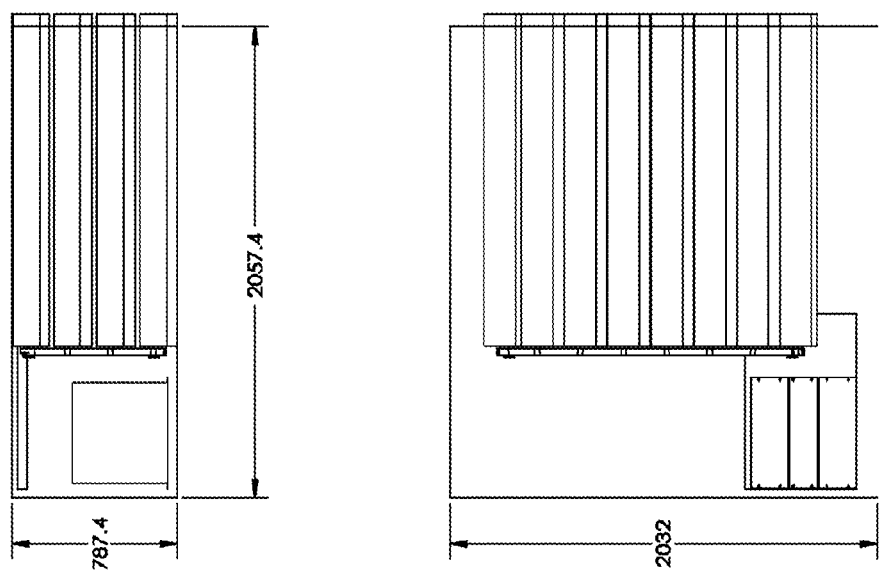
FIGURE 12D

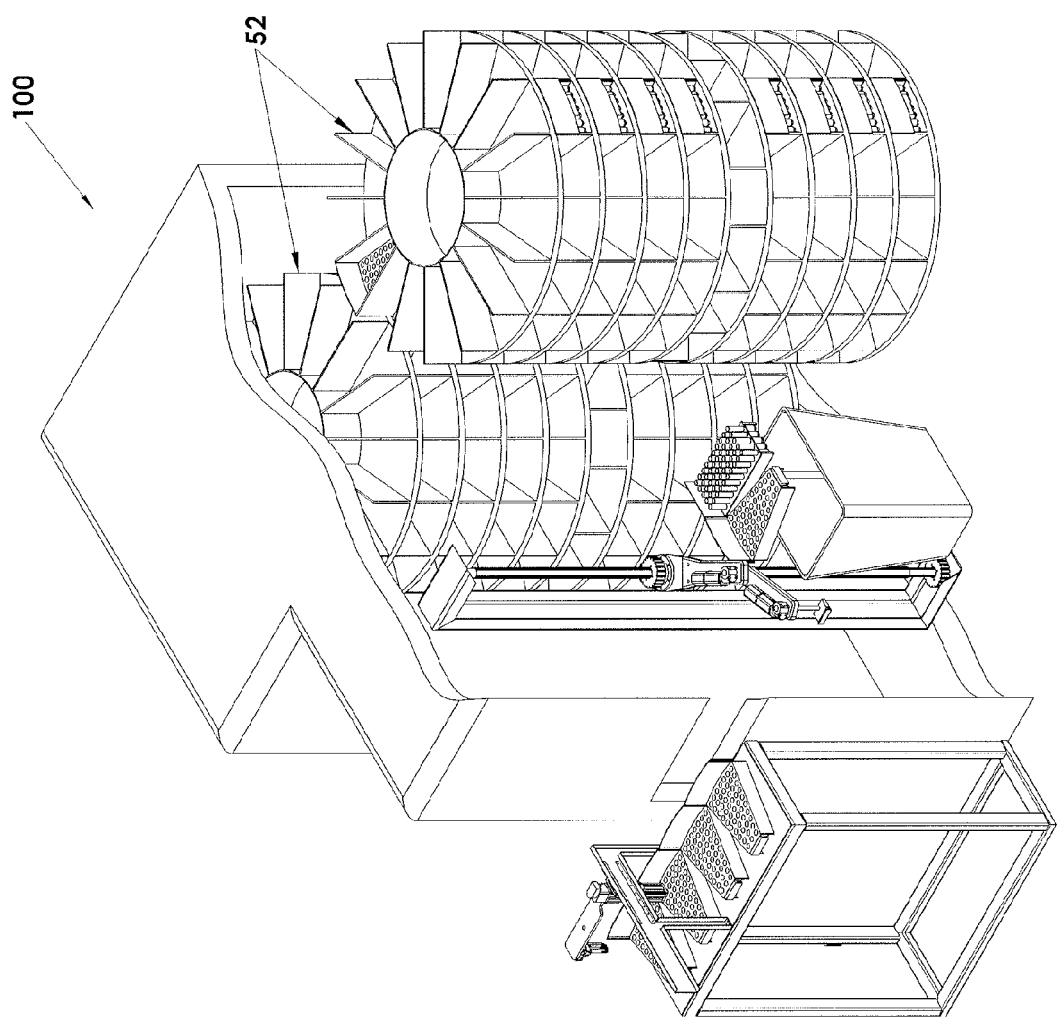

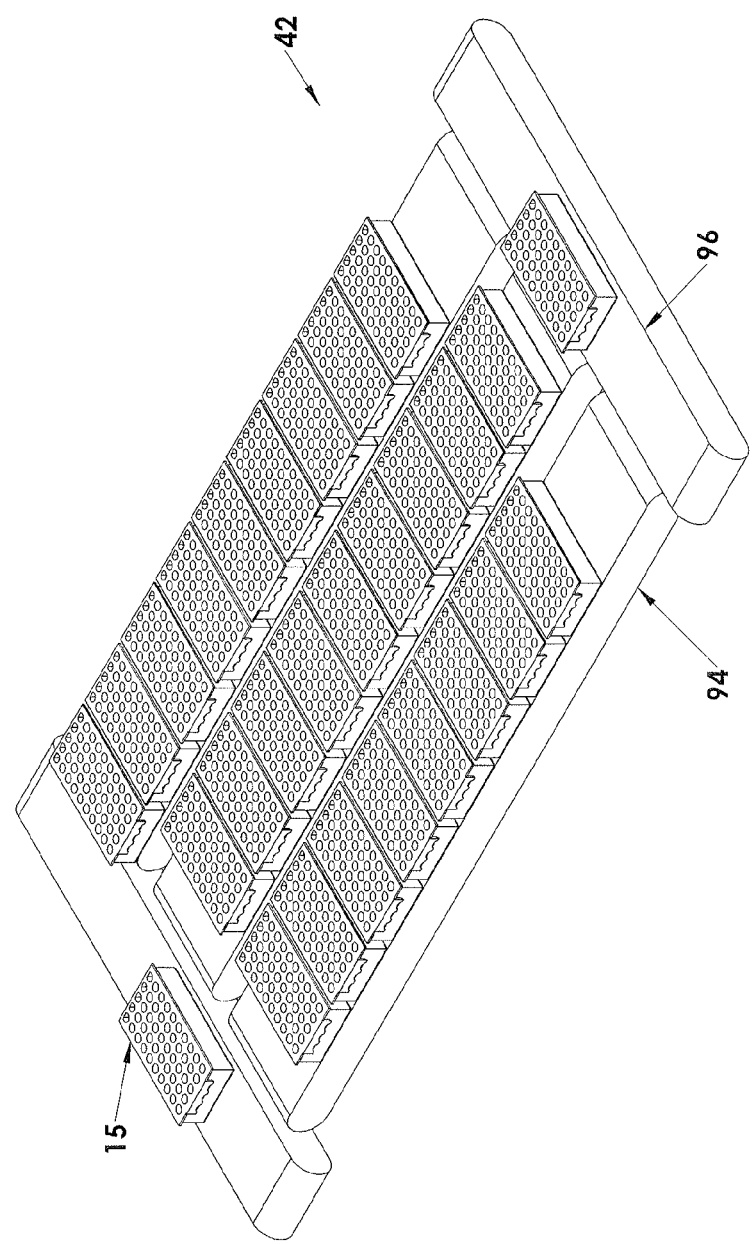
FIGURE: 14A

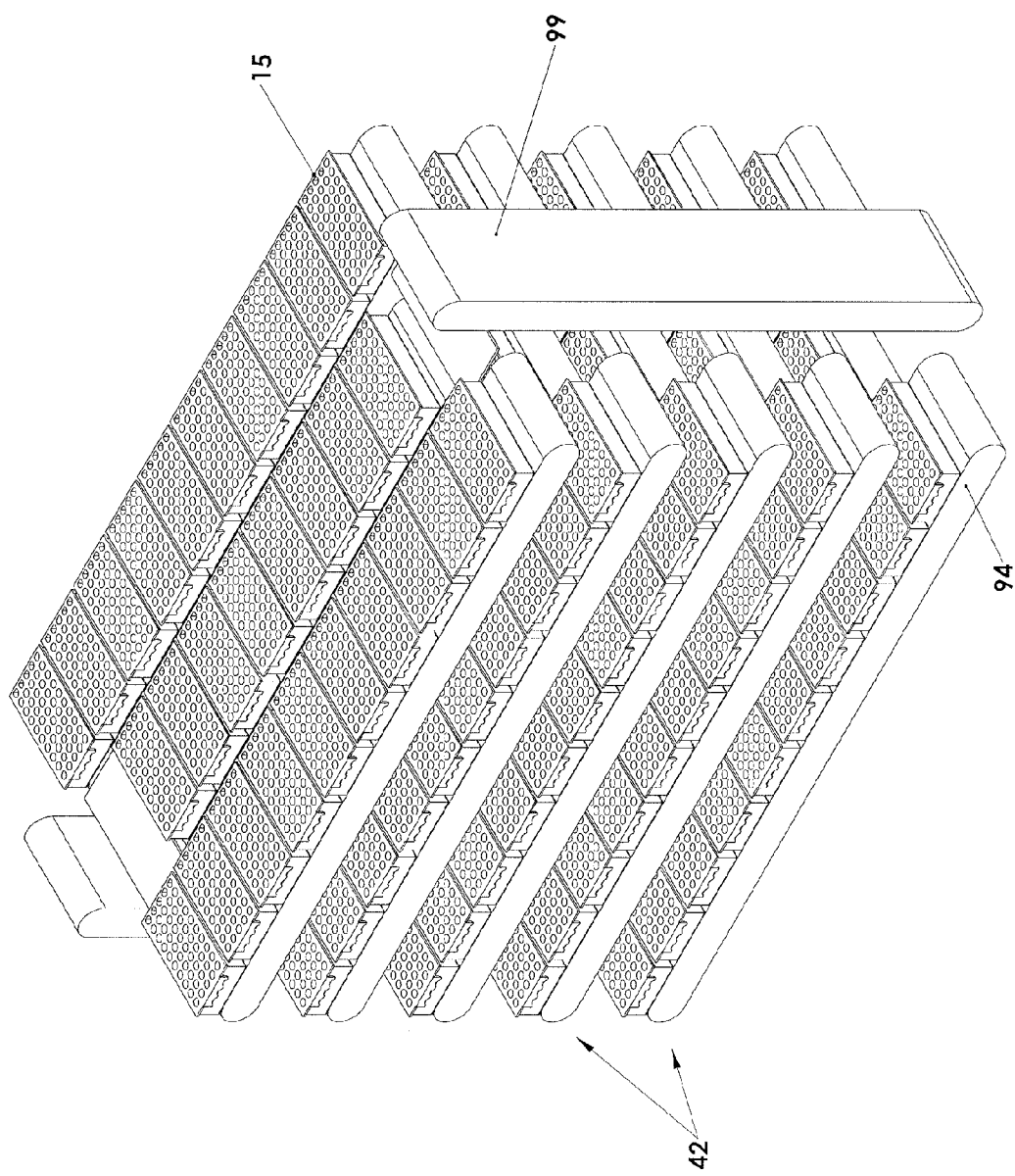
FIGURE: 14B

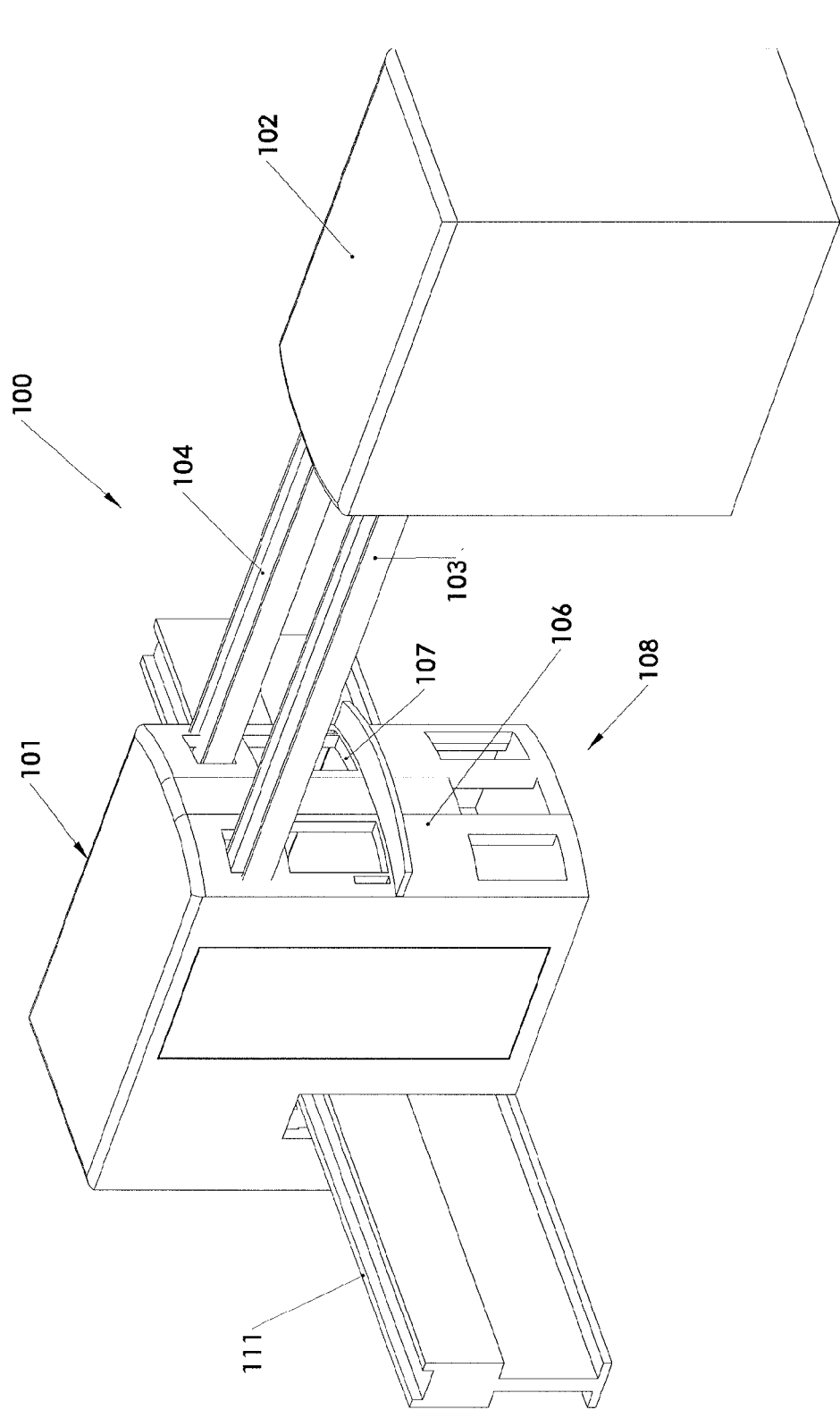
FIGURE: 15

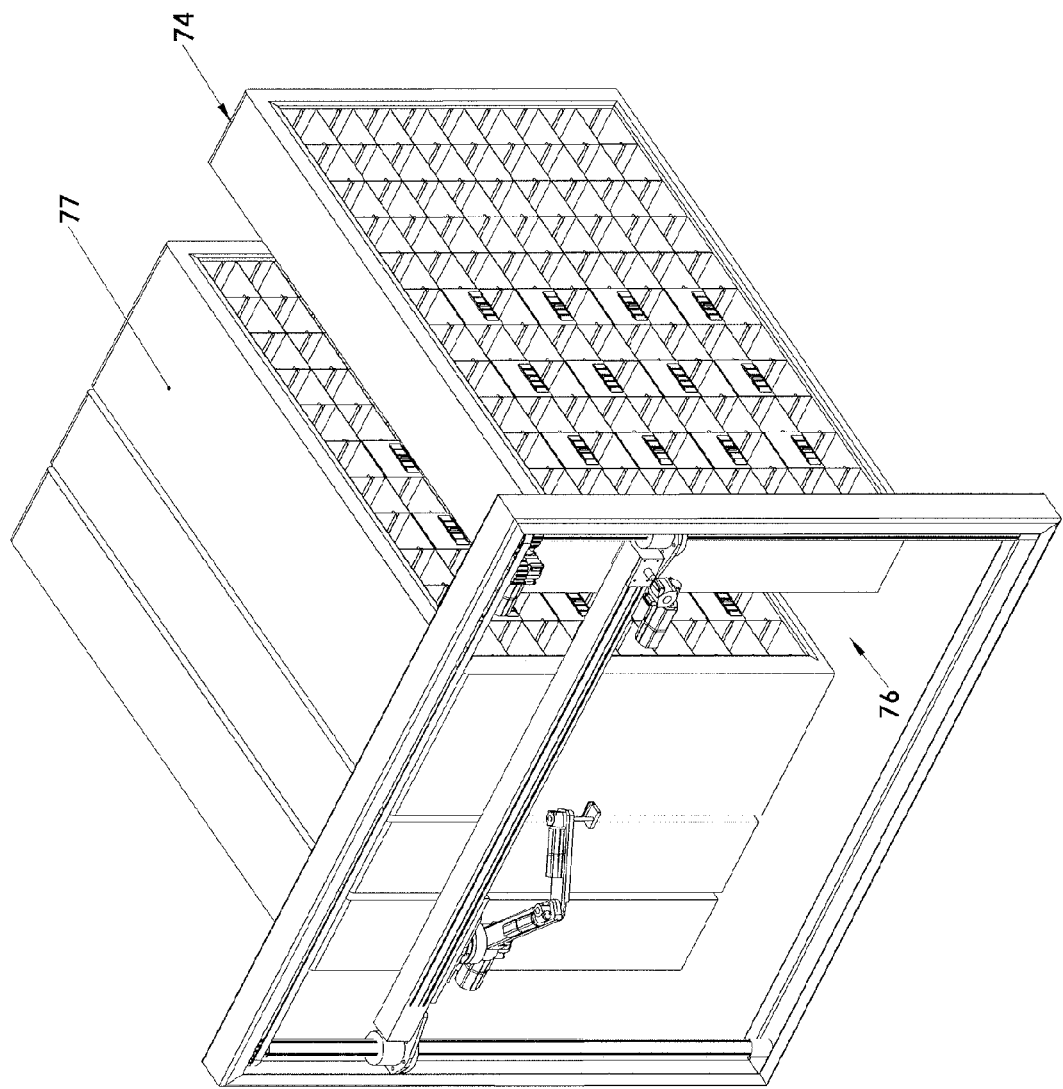

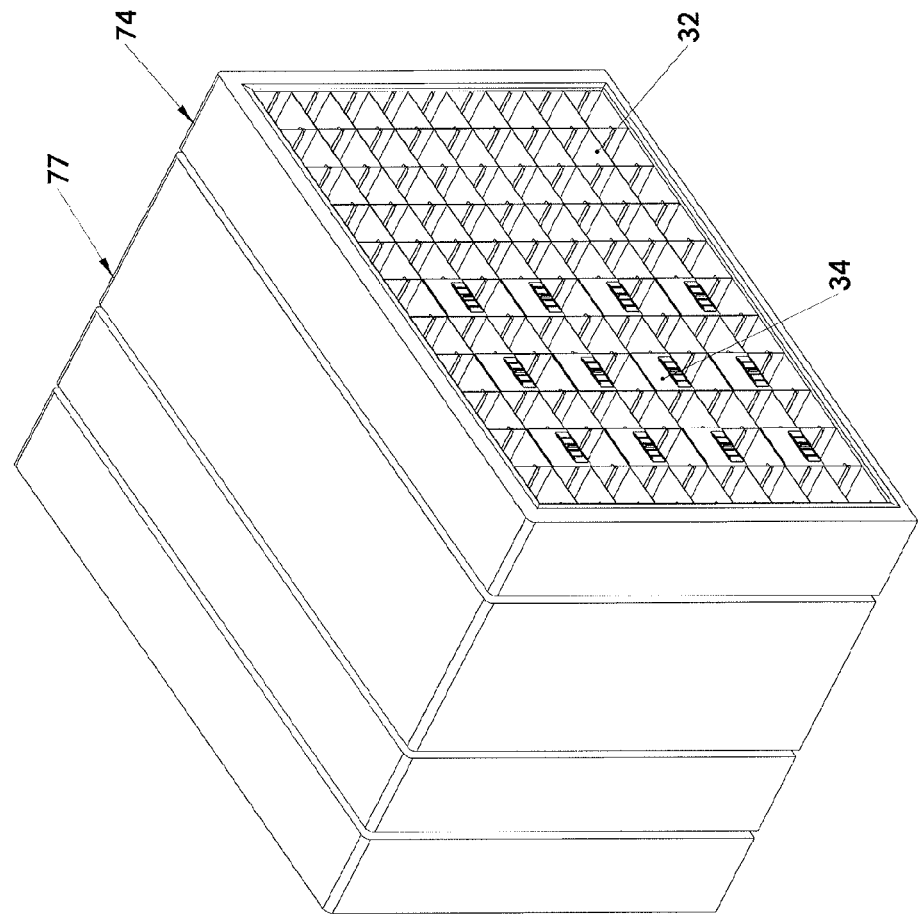
FIGURE: 17

AUTOMATED, REFRIGERATED SPECIMEN INVENTORY MANAGEMENT SYSTEM

CROSS-REFERENCE TO RELATED APPLICATIONS

This application claims the benefit of U.S. Provisional Application No. 61/263,842, which was filed on Nov. 24, 2009.

STATEMENT REGARDING FEDERALLY SPONSORED RESEARCH OR DEVELOPMENT

Not Applicable

BACKGROUND OF THE INVENTION

Laboratories that routinely analyze patient specimens have special needs related to the receiving, handling, and storage of samples/specimens once samples/specimens arrive at the laboratory in tubes/containers. Special handling and/or storage requirements are necessary prior to testing, i.e., "pre-analytical", between testing, and/or after testing, i.e., "post-analytical". Several of the special requirements impact the quality, accuracy, and/or precision of tests performed on human or animal samples/specimens. Other special requirements are aimed at safely disposing of the samples/specimens once all testing has been completed or the sample/specimen is no longer viable for use in testing.

The most common procedure used in a laboratory for all, or most, of the sample/specimens received is to initially leave the incoming samples/specimens exposed to the ambient room temperature. More particularly, samples/specimens typically remain at ambient temperature during two stages in the typical laboratory workflow. The first stage occurs while the sample/specimen is waiting to be analyzed and/or re-analyzed, which can take hours. The second stage occurs after testing has been completed during which samples/specimens are typically left exposed to the ambient room temperature, placed in a cooled waiting storage area, or disposed of, which occur either at the end of the current operating shift or at the end of the day.

The optimum temperature at which each sample/specimen should be stored prior to analysis varies by the type of test to be performed and/or by the type of sample/specimen, e.g., blood, serum, plasma, cerebral spinal fluid, urine, sperm, and so forth. Indeed, instruments that perform tests and/or the method sheet associated with the testing usually indicate an ideal temperature at which samples/specimens should be presented to the instrument for analysis. This complicates testing. For example, a sample/specimen stored in a refrigerated environment may have been stored at a temperature that is lower than the instrument desires, which could possibly produce inaccurate results. Conversely, a sample/specimen could be stored in a location that causes it to be warmer than desired for a specific instrument.

Accordingly, it would be desirable to provide an automated, refrigerated specimen management system (ARSIMS) having multiple controllable temperature zones to ensure that each sample/specimen arriving at a specific instrument arrives at the optimal or ideal temperature for the instrument according to the method sheet.

SUMMARY OF THE INVENTION

An automated, refrigerated specimen management system (ARSIMS) is disclosed. The ARSIMS is structured and arranged to hold sealed and/or opened sample/specimen tubes and/or containers that can be in the pre-analytical, in-process, or post-analytical phase of processing. Each sample/specimen tube, whether it is sealed, capped, closed or open, can be stored at an ideal storage temperature according to the particular phase of processing and as appropriate for the combination of sample/specimen type and analyte(s) to be tested.

Each sample/specimen can be stored, at any time and regardless of the phase, within the ARSIMS in an environment ranging from ambient room temperature to the temperature of the refrigerator and any temperature in between. In short, the ARSIMS is adapted to dynamically allocate the amount of pre-analytical and in-process storage space at a myriad of required temperatures necessary to handle each day's changing workload, out of the total available fixed amount of storage space within the sample storage portion of ARSIMS. Furthermore, optionally, pre-analytical and/or in-process storage space can be dynamically allocated between multiple, user-defined, enclosed temperature zones, wherein each temperature zone is made up of at least one tray bin, which can hold a single or a plurality of sample/specimen-holding trays.

The ARSIMS is also structured and arranged to minimize evaporation from occurring from samples/specimens being stored in open, i.e., unsealed, tubes, whether the sample/specimen is in the pre-analytical, the in-process, or the post-analytical phase of processing. Preventing or minimizing evaporation can be accomplished by placing open or unsealed tubes or containers in upper compartments in which a seal is created by the very close proximity and/or intimate contact between the properly-seated tray that physically holds the samples/specimens, and the tray bin that physically holds the tray(s).

Advantageously, the ARSIMSS is also capable of automatically and safely disposing of sample/specimen tubes into bio-hazard containers after and as soon as the sample/specimen or test specific storage time is exceeded.

The ARSIMS, which may or may not be connected to a larger system that is itself capable of automatically moving samples/specimens around a laboratory, is structured and arranged to accept or receive samples/specimens that are stored in tubes and/or containers as soon as the samples/specimens arrive in the laboratory and/or after the samples/specimens have been through the accessioning and/or receiving areas. If the ARSIMS is operatively coupled to a Laboratory Automation System (LAS), the samples/specimens can be accepted or received by the ARSIMS prior to their being placed on any track or conveyor portion of the LAS. The initial receipt/check-in of samples/specimens by the ARSIMS can occur prior to and/or after centrifugation.

Preferably, the samples/specimens can be loaded into the ARSIMS using any or a combination of a plurality of trays or other devices that are structured and arranged to hold a plurality of tubes and/or containers, single tubes and/or containers, a plurality of tubes and/or containers that have been dumped or placed into a hopper in batches or by an operator manually placing individual tubes into the ARSIMS.

Advantageously, the ARSIMS allows the user to define a plurality of unique, discrete enclosed temperature zones, in which the temperature and/or humidity can be set up to match the pre-analytical storage temperature requirement of a specific combination of sample/specimen type and/or tests. Each enclosed temperature zone can store one or a plurality of specimens/samples that are stored in one or more trays.

Each unique temperature setting is based on the type of sample/specimen and/or the test(s) that will next be run on the sample/specimen. Based on the type of sample/specimen and test requested the ARSIMS automatically stores the tube and/or container containing the sample/specimen in an appropriate enclosed, temperature- and/or humidity-controlled zone to wait for the next processing step, which can include, but is not limited to any of the following: the sample/specimen is automatically withdrawn from the zone to either be automatically placed on the LAS track for automatic delivery to an appropriate analyzer; placed in a Temperature Equilibration Area, which is an area within the ARSIMS at which samples/specimens are stored to reach a temperature equilibrium with the environment of the laboratory and/or to reach a temperature equilibrium required by a subsequent test; delivered to a special area from which an operator can manually remove the tubes and/or containers and either introduce the manually-removed sample/specimen to an instrument for analysis and/or safely placed in a sealable bio-hazard waste container for removal and eventual disposal.

The ARSIMS is capable of reading a bar code and/or RFID tag that is attached to each tube and/or container as soon as it is loaded into, or presented to, the ARSIMS by any of the previously described means. Accordingly, the ARSIMS is capable of determining where the coded tube and/or container is now and where it should be stored within the system before its next processing phase. The bar code reader(s) and/or RFID reader associated with checking in a new sample/specimen in a tube and/or container can be integrated into the ARSIMS or can be an external, stand-alone instrument. If external, the reader can be coupled to the ARSIMS using at least one of a hardwire, a fiber optic cable, a wireless connection, and so forth.

Advantageously, the ARSIMS is adapted to dynamically reconfigure, i.e., increase or decrease, the amount (volume) of storage space available for each desired temperature zone, to accommodate current, real-time sample/specimen storage requirements. A temperature zone can relate to at least one of an enclosed area, a tray bin, and the like. Each zone can be maintained at a unique temperature/humidity setting or multiple zones can be set to the same temperature/humidity setting at the same time.

Samples/specimens can be stored in individually-sealable sample/specimen tubes and/or containers, unsealed sample/specimen tubes and/or containers, and/or in trays of the same. An entire group of samples/specimens can be collectively covered and/or sealed by any one of a myriad of means that include, without limitation, individual tray covers, placing trays in enclosed/sealed tray bins, or placing trays in sealed upper compartments. The trays can be constructed of material having insulating properties to minimize thermal losses via conduction. The tray bins and/or optional tray bin door(s) can also be constructed of material having insulating properties.

The various embodiments of the ARSIMS include every size, shape, and capacity tray, as well as any size shape and capacity individual tray bin. The tray in combination with the tray bin and/or tray cover are designed to segment the tubes/containers into two compartments: a sealed upper compartment and a lower compartment. It is desirable to achieve an airtight seal or minimize air flow between the sealed upper compartment and the lower compartment when a tray is fully inserted into and properly seated within a tray bin. Preferably a top portion of the tray, which holds the tubes and/or containers, can be made of a solid material that prevents air from flowing from one compartment to the other. Alternatively, a tray liner that limits or eliminates air flow can be used to form the bottom of the sealed upper compartment.

The side of the tray can also be structured and arranged to form an air-tight seal with a pair of tray slides on the inner walls of the tray bin, which allows the tray to slide as it is pushed into or pulled from the tray bin. In another alternative, the front and/or rear faces of the tray can be structured and arranged to match the size and shape of a respective tray bin opening so as to limit the amount of uncontrolled air flow that enters the tray bin and to prevent air from reaching the sealed upper compartment from the lower compartment. It is desirable to achieve as close to an airtight seal as possible between the faces of the tray and the openings of the tray bin.

In an alternate embodiment, if one end of the tray bin has a solid face, only the face of the tray at the opposite end of the tray bin is needed to make an adequate air seal/barrier with the opening through which the tray is inserted into the tray bin. On the other hand, if the tray bin is open on both ends so that a first end is exposed to a first environment, which could either be a refrigerated or an ambient side, and the second end is exposed to a second environment, which differs from the first environment, the tray can have a front face and rear face, each of which must form an air seal/barrier with the corresponding opening in the tray bin.

In addition to providing support, the trays and/or tray bins can also contain one or more air vents and one or more manually- or automatically-controllable air registers. Manually or automatically moving the air registers, once a tray is inserted into and properly seated in the tray bin, controls the air flow into or out of the lower compartment. Advantageously, the temperature of each tray bin can be controlled by manually opening, closing or adjusting the air registers to control the amount of air at a given temperature that is at allowed to enter into the lower compartment of a tray bin. Adjustment of air registers can also be controlled by one or a plurality of a computer processor and/or discrete electronic components. Air registers affecting a single or a plurality of tray bins can be changed together or individually.

The air registers and/or air vents controlling the flow of air into the tray bin can be located on any one of or a combination of the six faces of a tray bin. In one embodiment of this invention the air registers and/or air vents are located on both the front and rear faces of the tray and tray bin.

The sealed upper compartment and lower compartment experience different amounts of airflow. The sealed upper compartment, which is disposed above the tray top, is the compartment in which air flow is eliminated or reduced, e.g., to minimize evaporation experienced by open tubes and/or containers held therein. The lower compartment, which is below the tray top, is structured and arranged to allow air to freely flow and to be exchanged to equilibrate the samples/specimens contained in the tubes and/or containers with the temperature of the air in the lower compartment.

Flow of the temperature-controlled cooling medium, e.g., air, water, gas, and like fluids, through the lower compartment can occur by at least one of passively or actively, e.g., pumping, facilitated movement of a fluid or by airflow, air convection, and the like, and actively facilitated movement/flow of air, e.g., using a fan, a blower, and the like. Air ducts can be provided to bring air either directly into or within an effective working distance of air vents and/or air registers that are disposed on any surface such as the front and/or rear faces of the tray and/or tray bin nearest the air ducts. Controlling and changing the temperature of the air flowing through air ducts within the ARSIMS can be used to control the individual temperature of the lower compartment(s).

When the tubes and/or containers are closed/sealed, the air registers and/or air vents can be located anywhere on the front or rear faces of the tray and are not limited to being below the tray top since in these cases there is no need to create or maintain separate upper and lower compartments.

Trays within tray bins do not have to form compartments that are purposely separated by an air seal or air barrier. Instead, air at specific controlled temperatures can flow over the entire length of the sealed or capped tube and/or container. However, air flow into and/or out of the tray bin(s) and/or tray(s) occurs via each of the mechanisms and descriptions provided for in each of the different embodiments or configurations involving a sealed upper compartment.

Preferably, the ARSIMS is adapted to support a master test menu and/or master sample/specimen type menu, within which the user identifies the desired pre- and post-analytical storage temperatures desired for each unique combination of sample/specimen type and test requested. The ARSIMS can also learn the ideal storage temperature for a given sample/specimen by querying the Laboratory Information System (LIS) to which the ARSIMS is coupled or from any other system capable of communicating with the ARSIMS.

The ARSIMS can also include at least one Temperature Equilibration Area (TEA). TEAs are used to allow samples/specimens, before they are placed on the track, to be brought from the temperature at which they were stored within the ARSIMS or before they are introduced into the ARSIMS to the temperature the analyzer is expecting the sample/specimen to be when it arrives for analysis. In addition to separate TEAs, the warm up and/or cool down of tubes and samples/specimens can be accomplished with a tray bin by bringing the temperature, at a controlled rate, from a first temperature, e.g., refrigerated, to a second temperature, e.g., ambient.

In addition to controlling the overall refrigerated temperature to the preset value at a multiplicity of locations, the ARSIMS can also control and maintain humidity to a preset value and/or can filter and/or clean the air used to cool or warm the samples/specimens.

Optionally, the ARSIMS can include a vision-based subsystem used to determine, for example, whether or not a tube is sealed, whether or not a tube is capped, whether or not a tube has been spun, whether or not the sample/specimen is lipimic, icteric, and/or hemolyzed, the quantity of useable sample/specimen still in a tube, the color of the top of the tube, and so forth.

A further advantage of the invention is that a user can define the period of time a sample/specimen remains on the system before it is automatically discarded. A unique period of time for storing a discrete sample/specimen can be established based on, for example, the type of sample, draw/collection site, draw/collection date/time, requesting doctor, test(s) performed on the sample/specimen, time the sample/specimen was first placed into the ARSIMS. Preferably, the ARSIMS automatically disposes of the tube/container in which the sample/specimen is stored when the designated storage time has elapsed based on the criteria applicable to each sample/specimen into a bio-hazard waste container.

BRIEF DESCRIPTION OF THE SEVERAL VIEWS OF THE DRAWINGS

Other features and advantages of the invention will be apparent from the following description of the preferred embodiments thereof and from the claims, taken in conjunction with the accompanying drawings, in which:

FIG. 10 shows an isometric view of an alternate dual shelving storage unit in accordance with the present invention;

FIG. 12A shows plan, isometric, and elevation views of an arcuate storage unit;

FIG. 12B shows plan, isometric, and elevation views of a peg board storage unit;

FIG. 12C shows plan, isometric, and elevation views of a dual Ferris wheel storage unit;

FIG. 12D shows plan, isometric, and elevation views of a single Ferris wheel storage unit;

FIG. 13 shows an automated, refrigerated specimen inventory management system having two multilevel specimen carousels in accordance with the present invention;

FIG. 14A shows a plan view of a representative level of a multilevel shuttle-type storage unit;

FIG. 14B shows an isometric view of a multilevel shuttle-type storage unit;

FIG. 15 shows a split storage unit in accordance with the present invention;

FIG. 16 shows an isometric view of a movable bookcase-type storage unit; and

FIG. 17 shows an isometric view of the movable bookcase-type storage unit shown in FIG. 16 in a closed state without a space between shelves.

DETAILED DESCRIPTION OF PREFERRED EMBODIMENTS OF THE INVENTION

U.S. Provisional Application No. 61/263,842, from which the benefit of priority is claimed, is incorporated herein in its entirety by reference.

An automated, refrigerated specimen inventory management system (ARSIMS) for holding a plurality of containers containing a sample/specimen under test, e.g., in a pre-analytical phase, in an in-process phase, and/or in a post-analytical phase of processing, is disclosed. The ARSIMS holds the containers in discrete temperature- and/or humidity-controlled zones, which are maintained at a storage temperature appropriate for the testing and the phase of processing of the tubes and/or containers stored therein. The ARSIMS includes a temperature control unit, a plurality of sample- or specimen-containing tubes and/or containers, a tube and/or container receiving and removal area, an area(s) having a plurality of controllable temperature zones, each zone structured and arranged to hold a discrete number of the tubes and/or containers at a desired, controlled temperature and/or controlled humidity; a temperature equilibration area; and a controller.

The temperature control unit produces a cooling or warming fluid having a controlled temperature and/or controlled humidity to selected locations. The container receiving and removal area is structured and arranged for inserting tubes and/or containers into an appropriate temperature- and/or humidity-controlled area commensurate with the sample/specimen contained therein and the phase of processing as well as for removing containers from the temperature- and humidity-controlled area for disposal or for analysis. The temperature equilibration area is adapted to enable tubes and/or containers to reach a temperature equilibrium commensurate with a temperature at a next destination. The controller is adapted to controlling the movement, location, and storage temperature of each of the plurality of tubes and/or containers; to automatically and dynamically create discrete controlled temperature zones for storing tubes and/or containers together at a common temperature; as well as to control all of the other functional elements of the system.

Although the invention will be described using air as the fluid, the fluid could also be a liquid or a gas or mixture of gases. When the fluid is a liquid, any feature that is described hereinbelow as being airtight or as providing an airtight seal would also have to be watertight or provide a watertight seal.

Tray Bins and Sample/Specimen Trays

Referring to FIGS. 3A-3G, FIGS. 5A-5D, and FIGS. 7A-7G, various embodiments of tray bins 10 and trays 15 will be described. Tray bins 10 are discrete locations in the ARSIMS 100 that are structured and arranged to hold a tray 15 that holds a plurality of capped or uncapped, covered or uncovered, open or closed, sample/specimen-containing tubes and/or containers 20.

Figure 1:
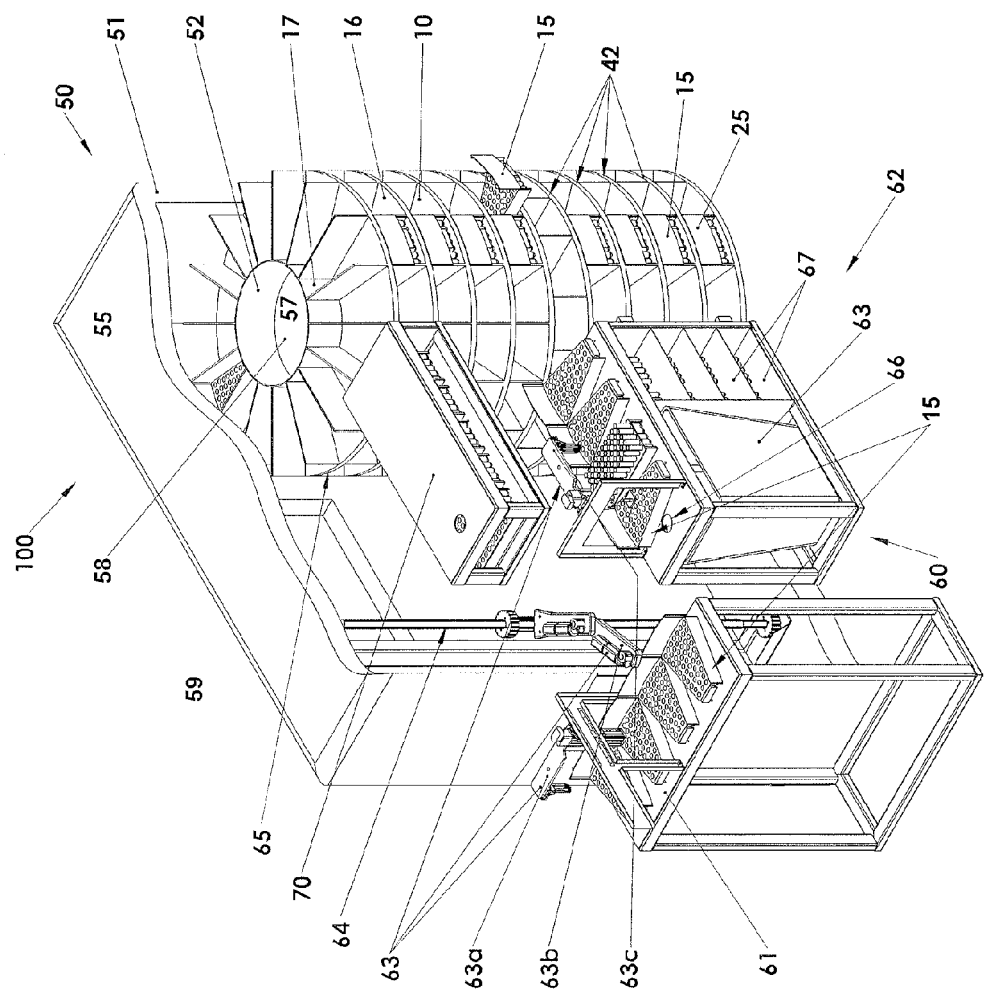
FIG. 1 shows an automated, refrigerated specimen inventory management system having multilevel specimen carousel storage in accordance with the present invention.
Figure 3A:
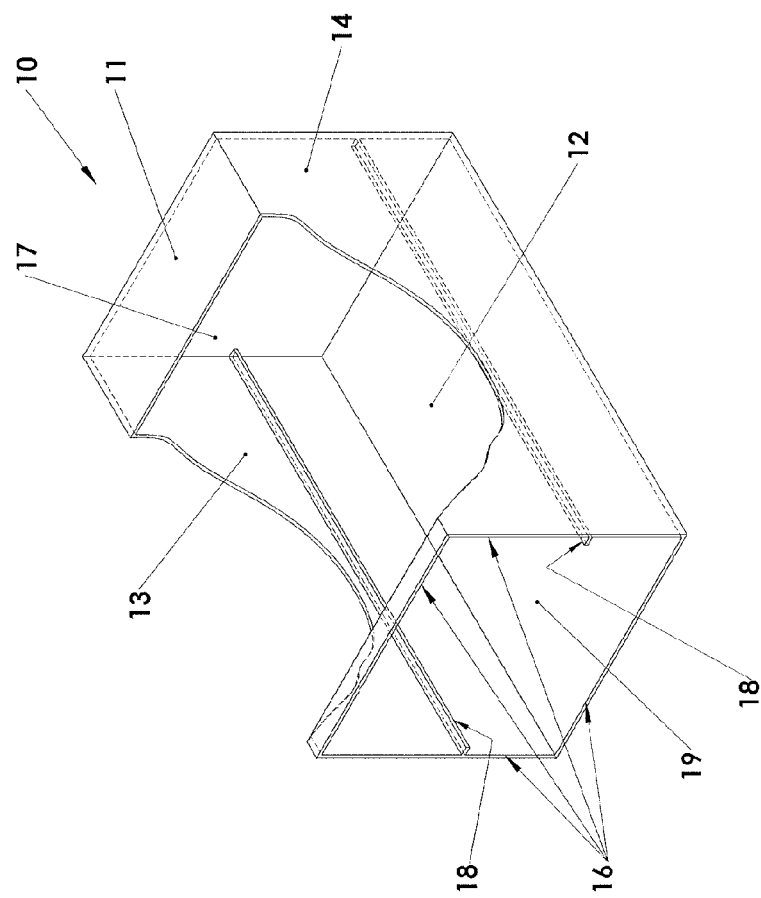
FIG. 3A shows a tray bin with a front opening, a solid rear wall, and tray slides.
Figure 5A:
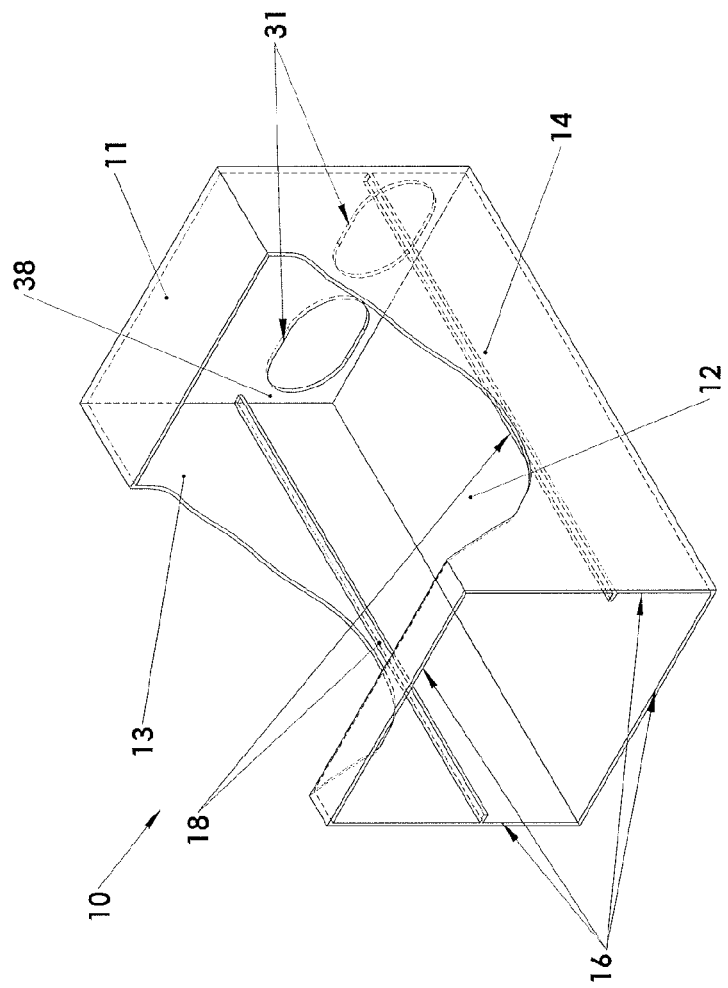
FIG. 5A shows a tray bin with a front opening, a vented rear wall, and tray slides.
Figure 7A:
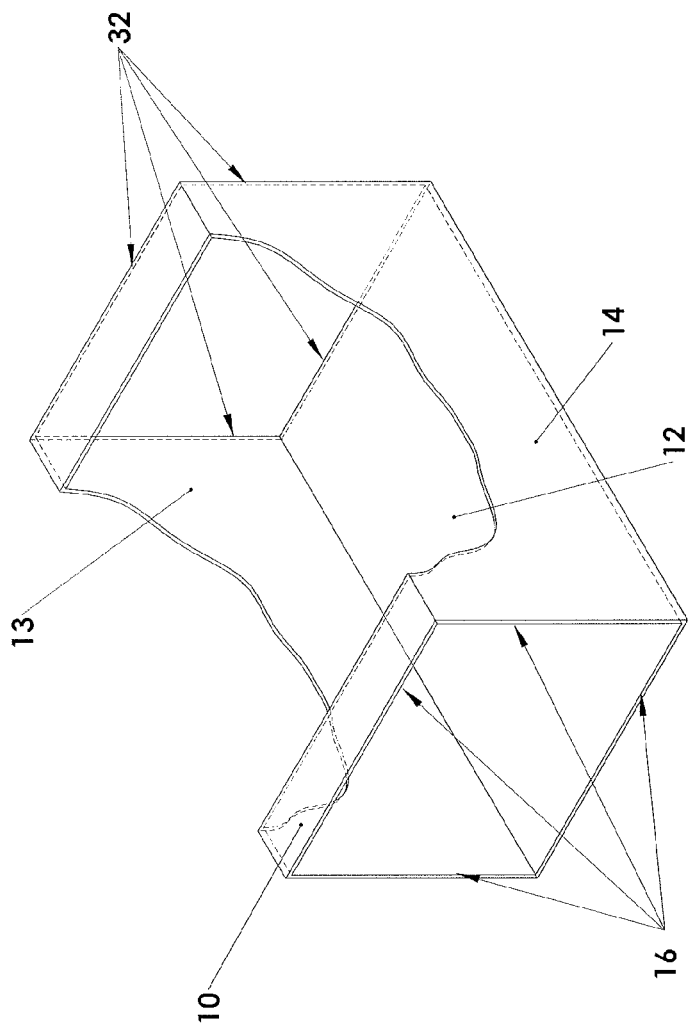
FIG. 7A shows a tray bin with a front opening and a rear opening.

FIGS. 3A, 5A, and 7A show partial cut away isometric views of possible embodiments of a single tray bin 10. Although the tray bin 10 is shown to have a generally rectangular shape, the invention is not to be so limited. Indeed, as shown in FIG. 1, the tray bins 10 can have a trapezoidal shape, an arcuate shape, and so forth. Furthermore, although the tray bins 10 are shown as accommodating a single tray 15, the invention is not to be so limited. Indeed, the tray bins 10 can be structured and arranged to hold one or a plurality of trays 15.

Tray bins 10 can be manufactured or assembled as an integral part of the storage unit of which it is part, for example a left shelving unit, a right shelving unit, a sample carousel storage unit, and so forth, which will be described in greater detail below. Alternatively, tray bins 10 can be insertable into and removable from the storage unit.

Tray bins 10 include a top portion 11 (which is cut away in the figures), a bottom portion 12, a left side wall 13, and a right side wall 14. FIG. 3A shows a front opening tray bin 10 that includes an open front end 16, through which a tray 15 can be inserted or removed, and a rear wall 17. The tray bin 10 in FIG. 3A includes a solid rear wall 17, to fully enclose and isolate the tray(s) 15 after they have been inserted. Advantageously, a solid rear wall 17 allows little or no air flow into the inner portion 19 of the tray bin 10.

Optionally, FIG. 3A includes a pair of tray slides 18, e.g., rails, that are optionally formed on or mounted inside of the tray bin 10 on inner surfaces of the left 13 and right side walls 14. FIG. 3F shows a tray bin 10 that does not include a pair of tray slides. Tray slides 18 are provided to facilitate the placement and movement of the tray 15 when inserted into or removed from the inside portion 19 of the tray bin 10. They also form part of an airtight seal between a lower compartment 28 and a sealed upper compartment 29. Although, the tray slide 18 is shown as a pair of rails, this is done for illustrative purposes only. Tray slides 18 can include several components, parts or structures that, with the tray top 21 of the tray 15, separate a tray bin 10 into a sealed upper compartment 29 and a lower compartment 28.

Figure 3C:
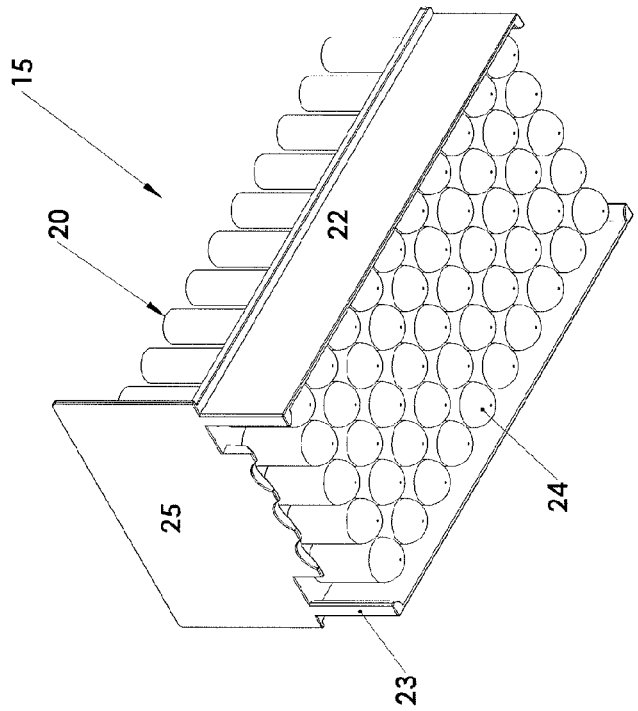
FIG. 3C shows a bottom isometric view of a tray having a solid front face and an open rear face for the tray bin shown in FIG. 3A.
Figure 3B:
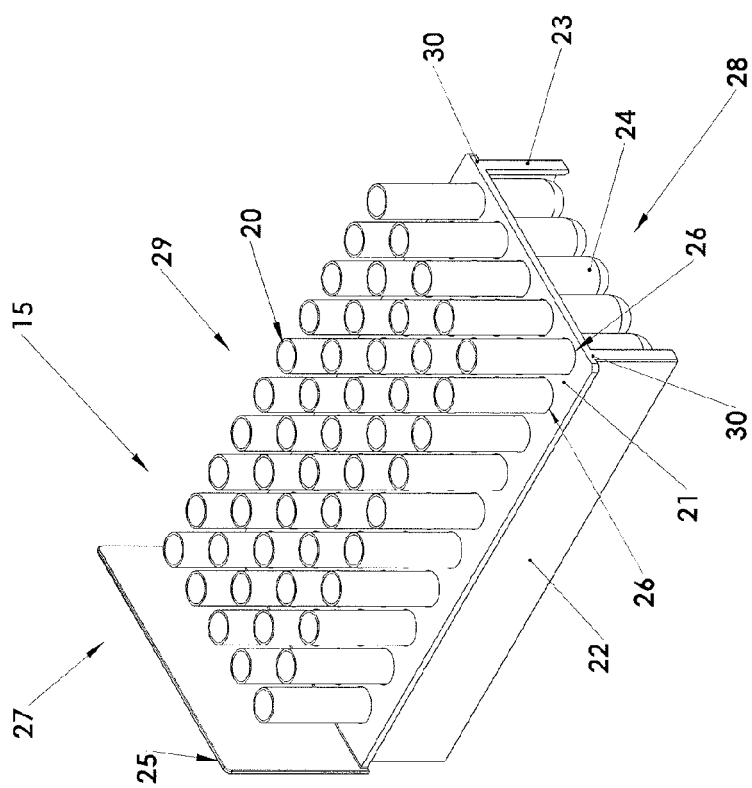
FIG. 3B shows an isometric view of a tray having a solid front face and an open rear face for the tray bin shown in FIG. 3A.

Representative solid front face trays 15 are shown in FIGS. 3B and 3C. Although these figures show that the trays 15 have the capacity to hold 50 tubes and/or containers 20, the invention is not to be construed as being so limited as the trays 15 can be manufactured to hold more or less than 50 tubes and/or containers 20. The trays 15 can have any shape, size, and/or tube capacity as long as the shape and size are compatible with the inner portion 19 of the tray bin 10. Those of ordinary skill in the art can appreciate that tray bins 10 can also be dimensioned to hold more than one tray 15.

The tray 15 shown in FIGS. 3B and 3C includes a tray top portion 21 that provides a plurality of openings 26 having a corresponding plurality of tray wells 24, which are structured and arranged to receive and to retain at least one sample/specimen-containing tube and/or container 20. The tray 15 also includes a solid front face 25, that is structured and arranged at a first, front end 27 of the tray 15. The tray top portion 21 and solid tray front face 25 are structured and arranged to provide two separate areas (or compartments) when the tray 15 in inserted into the inner portion 19 of a tray bin 10: a sealed upper compartment 29 and a lower compartment 28.

The sealed upper compartment 29 operates to minimize or eliminate fluid, e.g., air, flow into the sealed upper compartments 29. This isolation prevents or minimizes undesirable evaporation from uncapped, open, and/or uncovered tubes and/or containers 20. The lower compartment 28, on the other hand, is adapted to promote free fluid flow, to control the temperature and/or humidity of the samples/specimens contained in the tubes and/or containers 20 that are stored in the tray 15. Preferably, temperature is controlled by fluid convection of a cooling fluid; hence, by increasing fluid flow, the temperature in the lower compartment 28 decreases and by decreasing fluid flow, the temperature in the lower compartment increases. Because the sealed upper compartment 29 is airtight, the impact of the cooling fluid is reduced.

The openings 26 in the tray top 21 and the wells 24 are structured and arranged to hold tubes of various sizes and/or containers of any shape and/or size. The tubes and/or containers 20 shown in the wells 24 in FIGS. 3B and 3C are shown as "open tubes", which is to say that the tubes 20 are without caps or covers on the tops of the tubes 20 or without seals on the tops of the tubes 20. The sealed upper compartment 29 is adapted to prevent or minimize evaporation from open tubes 20. "Closed tubes" 20, e.g., tubes that are capped, sealed, or resealed, can also be used. Advantageously, if the closed tube 20 is airtight, it is not necessary to form or create a sealed upper compartment 29 with the tray 15 in the tray bin 10. However, it is still necessary to control and regulate the fluid flow, e.g., air, circulating at a controlled temperature within the inner portion 19 of the tray bin 10.

Figure 3E:
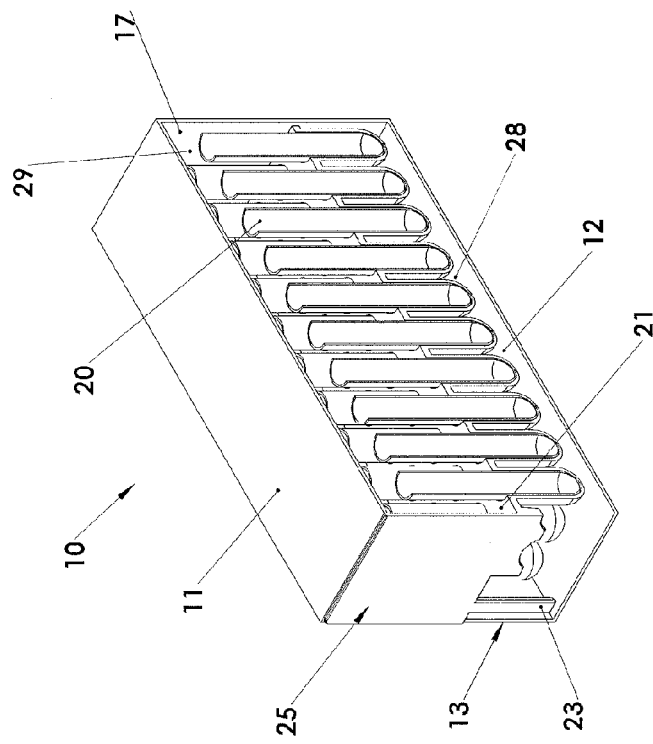
FIG. 3E shows an isometric sectional view of FIG. 3D.
Figure 3D:
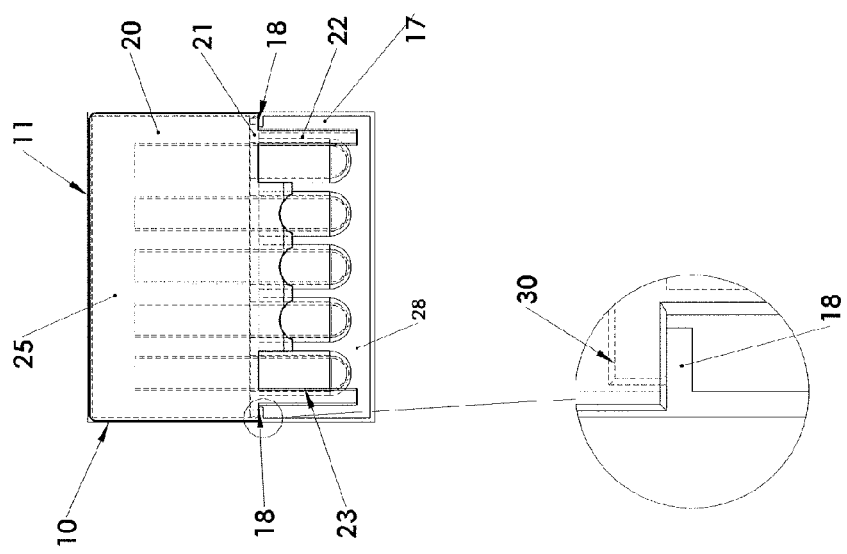
FIG. 3D shows the tray of FIGS. 3B and 3C inserted into and seated in the tray bin of FIG. 3A.
Figure 3G:
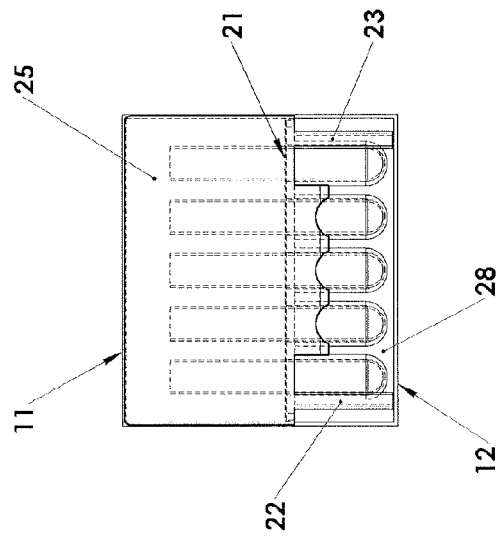
FIG. 3G shows the tray of FIGS. 3B and 3C inserted into and seated in the tray bin of FIG. 3F.
Figure 3F:
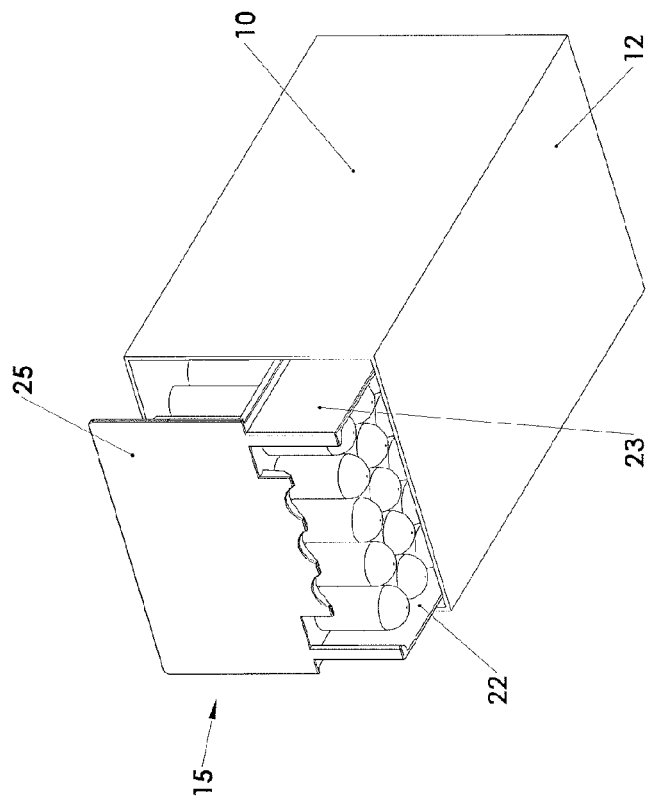
FIG. 3F shows a bottom isometric view of the tray of FIGS. 3B and 3C partially inserted into a tray bin without tray slides.

In addition to separating the tray 20 into two compartments 28 and 29 when the tray 15 is inserted into the inner portion 19 of the tray bin 10, the tray top 21 provides means for structurally supporting the tray 15 and the tubes and/or containers 20 inside and outside of the tray bin 10. For example, the left and right tray side walls 22 and 23 are structured and arranged so that they are longer than the wells 24 are deep so that the tray side walls 22 and 23 support the tray 20 when it is placed on a flat or planar surface. As shown in FIGS. 3F and 3G, the tray side walls 21 and 22 can also be used to support the tray 20 when it is inserted into the inner portion 19 of the tray bin 10. Alternatively, as shown in FIGS. 3D and 3E, flanged portions 30 of the tray top 21 can be provided to slide along the pair of rails 18 formed or mounted on the inside surfaces of the side walls 13, 14 of the tray bin 10. When the latter is the case, the mating portions of the pair of rails 18 and the flanged portions 30 should be structured and arranged to provide a substantially airtight seal between the two compartments 28 and 29, when the two are in intimate contact.

Although the shape of the tray 15 rear face is shown as U-shaped, this is for illustrative purposes only. The tray rear face can be of any size, shape, and/or height provided that when the tray 15 is fully inserted and properly seated within the tray bin 10, the tray rear face and/or the rear surface of the tray top 21 abuts the solid rear wall 17 of the tray bin 10 in such a way as to form a seal or connection that is capable of eliminating or reducing fluid flow between the tray rear face (not shown) and/or the rear face of the tray top 21 and the solid rear wall 17 of the tray bin 10.

The tray top 21, tray wells 24, and overhanging or flanged portions 30 of the tray top 21 are manufactured from material that can prevent fluid, e.g., air, from flowing from the underside of the tray 15, i.e., from the lower compartment 28, through the tray top 21 and/or tray wells 24 to the top side of the tray 15, i.e., the sealed upper compartment 29.

Optionally, trays 10 can include a removable, washable, or disposable tray liner (not shown). A tray liner facilitates cleaning the tray 15 and the tray wells 24. In order to capture and contain potential spills the tray liner may be impervious to liquids, which would also make it capable of eliminating or significantly reducing air flow through the tray liner. Accordingly, when a tray liner that is capable of eliminating or significantly reducing fluid flow from the lower compartment 28 to the sealed upper compartment 29 is used, the tray top 21 and/or the tray wells 24 can be constructed of lighter and/or non-solid material, and/or wire racks. The tray liner is adapted to entirely or partially cover the flat portion of the tray top 21, as well as to be able to fit down into the tray wells 24, in such a way as to allow tubes and/or containers 20 to fit properly inside the liner-filled wells 24.

FIGS. 3D-3G show the juxtaposition of trays 15 with respect to tray bins 10. Although the figures show the case in which the rear face of the tray 15 is inserted into the inner portion 19 of the tray bin 10 first, it is equally feasible to insert the first, front end 27 of the tray 15 first. The portion of the tray front face 25 above the tray top 21 is also designed to minimize or eliminate any fluid from flowing through it.

The overall size, shape, and edges of the tray front face 25 are designed and dimensioned to provide a tight fit with the front opening 16 of the corresponding tray bin 10, so as to minimize or eliminate fluid flowing between the portion of the tray 15 located above the tray top 21, i.e., the sealed upper compartment 29, and the corresponding lower compartment 28 once the tray 15 is fully inserted and properly seated in the inner portion 19 of the tray bin 10. At least a portion, if not all, of the first, front end 27 of the tray 15 that is located below the tray top 21 is open so that air at a controlled temperature and a controlled rate of flow can enter the lower compartment 28 for the purpose of bringing the lower compartment 28, including the bottom portion of the wells 24, the tubes and/or containers 20 contained in the wells 24, and the sample/specimen contained in the tubes and/or containers 20 to the desired temperature.

Any or all of the described tray components or structures can be manufactured as part of a single molding operation. Alternatively the tray components can be built from any combination of discrete components, all, some, or none of which, are molded parts.

Various surfaces and/or edges of various components, parts, portions, and/or structures of combinations of tray 15, tray bin 10, tray cover, and/or tray slides 18 can contribute, in different ways, to the formation and/or creation of one or a plurality of sealed upper compartments 29. A sealed upper compartment 29 is a three-dimensional compartment in which one or a plurality of open, uncapped, and/or unsealed tubes and/or containers 20 are stored, to prevent or minimize evaporation of the samples/specimens and/or analyte, diluent, and the like contained therein. Each edge and/or surface of the sealed upper compartment 29 provides a fluid flow barrier (not shown), which contributes to eliminating and/or restricting the flow of fluid into and/or out of the sealed upper compartment 29. In addition to touching or coming close to each other, the mating surfaces and/or edges that form the sealed upper compartment 29 can include rubber seals and/or some other sealing and/or latching mechanism (not shown) which provides additional protection against fluid flowing from the lower compartment 28 into the sealed upper compartment 29.

Figure 4:
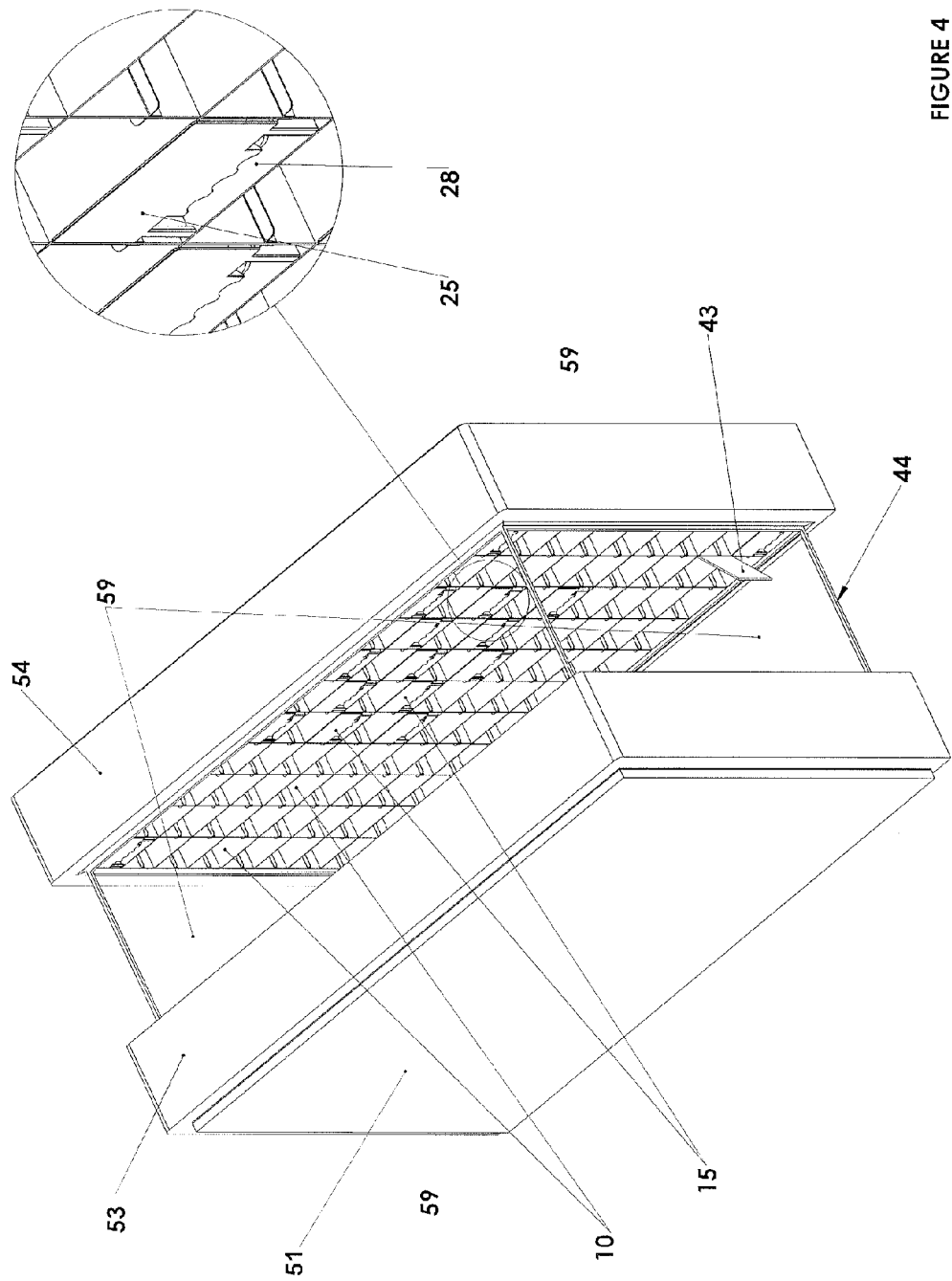
FIG. 4 shows an automated, refrigerated specimen inventory management system having dual shelving storage in accordance with the present invention.

As will be described in greater detail below, once a tray 15 is fully inserted into and properly seated within a tray bin 10, the temperature control unit of the ARSIMS 100 generates a temperature- and/or humidity-controlled fluid that circulates into and out of the lower compartment 28 through the opening(s) located below tray top 21 at the first, front end 27 of the tray bin 10. Alternatively, when the tray front portion 27 is inserted into the inner portion 19 of the tray bin 10 first, the rear end of the tray bin 10 can be sealed using, for example, a tray bin door 43 (FIG. 4). The tray bin door 43 can be opened to allow insertion or removal of a tray 15. When the tray bin door 43 is closed against the opening of the front opening 16 of the tray bin 10, the door 43 becomes another component or structure or edge that can form or can be used to form a sealed upper compartment 29. In instances in which tray bin doors 43 are used to seal or to form a fluid flow barrier with a tray bin 10, the length of the tray 15 should be such that the tray bin door 43 can be closed tightly enough, to form a seal or fluid flow barrier capable of minimizing or eliminating fluid flow into the sealed upper compartment 29.

Preferably, a portion of the tray bin door(s) 43 includes an opening below the level of the tray top 21, to allow a fluid at a controlled temperature and/or humidity, to enter, exit, and circulate through the lower compartment 28 of the tray bin 10. For example, air vents with or without air registers can be provided in the portion of the tray bin doors 43 below the level of the tray top 21. Optionally, tray bin doors 43 can be provided at both ends of the tray bin 10.

FIGS. 5A-5D show a second embodiments of a tray bin 10. The embodiment differs from the tray bin 10 shown in FIGS. 3A-3G only in that the solid rear wall 17 of the tray bin 10 is been replaced by a vented rear wall 38 having an air vent(s) 31. Accordingly, only the vented rear wall 38 and air vent(s) 31 need be described further.

Figure 5C:
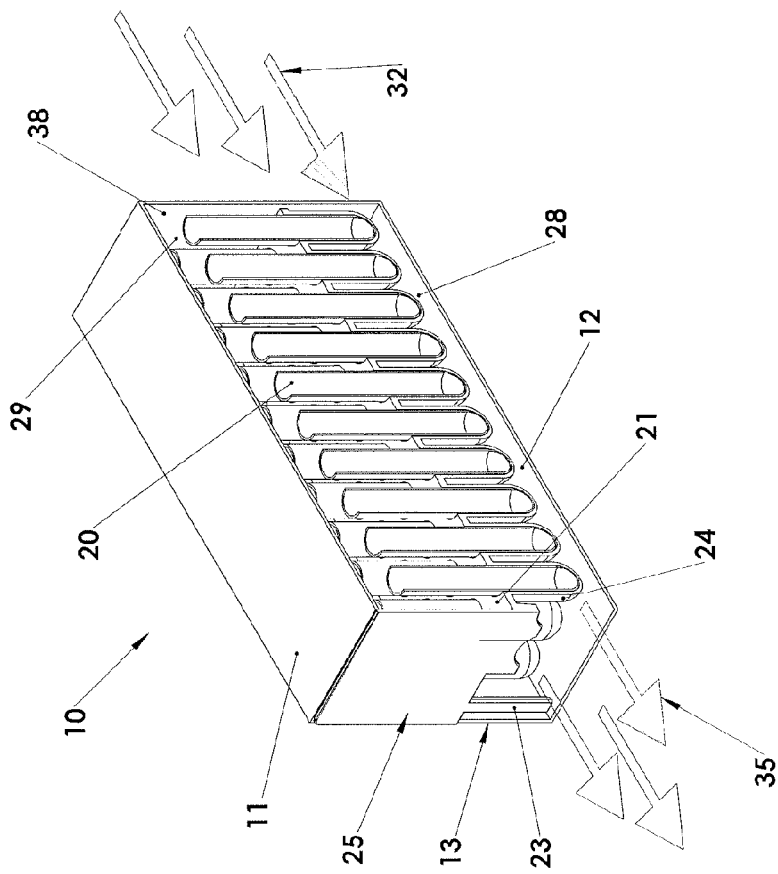
FIG. 5C shows an isometric sectional view of FIG. 5B.
Figure 5B:
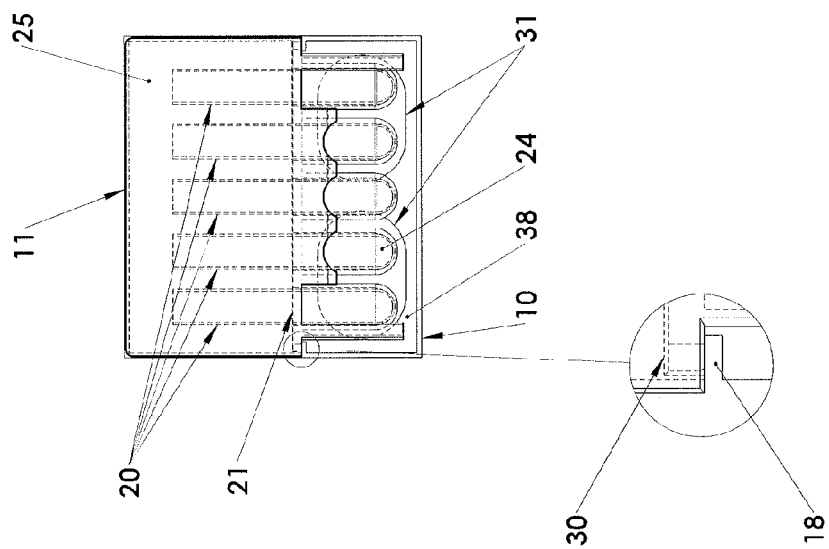
FIG. 5B shows the tray of FIGS. 3B and 3C inserted into and seated in the tray bin of FIG. 5A.
Figure 5D:
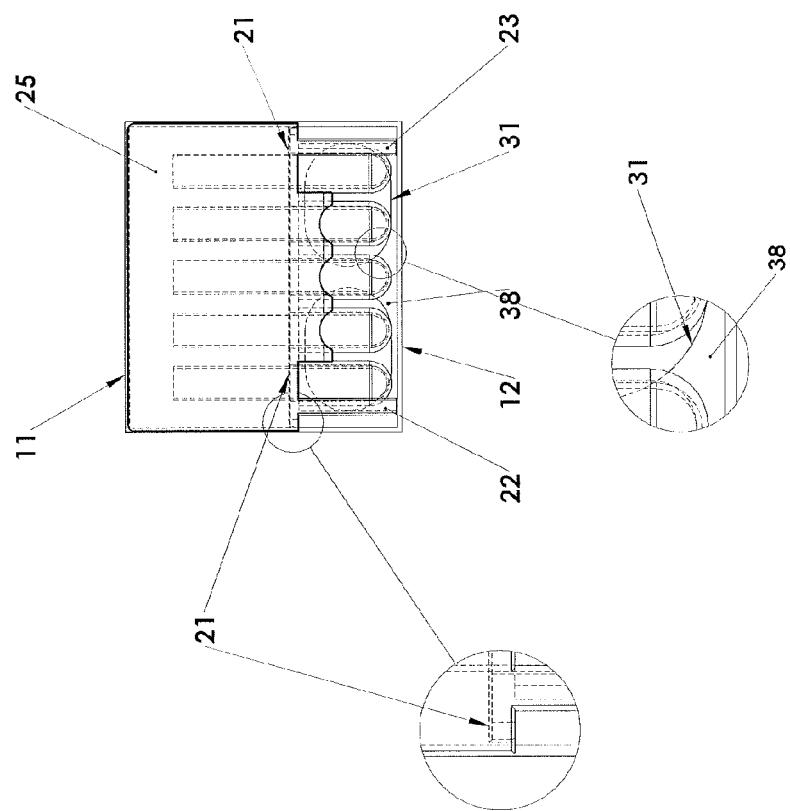
FIG. 5D shows the tray of FIGS. 3B and 3C inserted into and seated in the tray bin without tray slides.

Air vents 31 can be of any size, shape or combination of sizes and shapes. As shown in FIG. 5C, the air vent(s) 31 is/are disposed in the vented rear wall 38 so as to be below the level of the tray top 21 when a tray 15 is fully inserted and properly seated in the tray bin 10. Preferably, the air vent(s) 31 fluidly couple a fluid path 41, e.g., an air duct or conduit, with the lower compartment 28 of the tray bin 10, so that the fluid can enter, circulate therethrough, and exit as exhaust 35. Although FIG. 5C shows air circulating from the vented rear wall 38 towards the front opening 16 of the tray bin 10 and the front end 27 of the tray 15, those of ordinary skill in the art can appreciate that the fluid could just as easily circulate in the opposite direction, which is to say, entering at the front opening of the tray bin 10 and exhausting through the air vent(s) 31.

Optionally, a manually- or automatically-controllable air register (not shown) can be mounted onto the vented rear wall 38 of the tray bin 10, to selectively wholly or partially cover the air vent(s) 31, to control the flow of a fluid at a desired, controlled temperature and/or humidity into the lower compartment 28 of the tray bin 10. The controller of the ARSIMS 100 can be adapted to control air registers that are mounted on the rear walls 38 of the tray bin 10 individually or in groups. Air registers will be described in greater detail immediately hereinbelow.

A further embodiment of a tray bin 10 and corresponding tray 15 is shown in FIGS. 7A-7G. The tray bin 10 shown in FIGS. 7A-7G differs from previous tray bins 10 in that there is both a front opening 16 and a rear opening 32; so, as a result, there is no solid rear wall 17 or vented rear wall 38. Consequently, in order to provide two compartments 28 and 29 when a tray 15 is fully inserted and properly seated in the inner portion 19 of the tray bin 10, the tray 15 includes a vented front face 33 and a vented rear face 34 that each have an air vent(s) 31 that can be manually- or automatically-covered and selectively partially or fully covered via an air register(s) 37.

The front and rear faces 33 and 34 are identical or substantially identical so as to be interchangeable or not. More preferably, in order for the tray 15 to slide more easily within the tray bin 10, while still forming a seal and/or barrier to air flow between the rear face 34 of the tray 15 and the rear opening 32 of the tray bin 10, and, furthermore, in order for the front face 33 to form a seal and/or barrier to air flow at the front opening 16, the latter 33 should be slightly larger than the former 34.

Figure 7F:
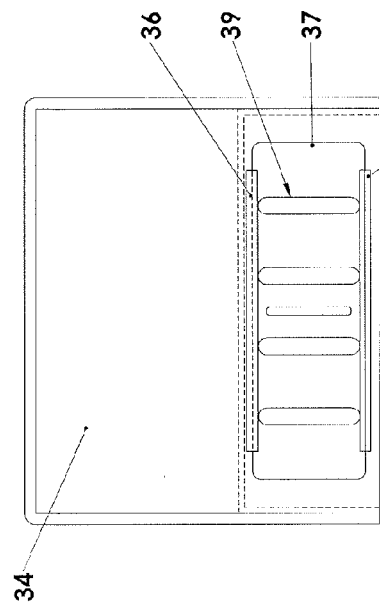
FIG. 7F shows an elevation view of the rear face and air regulator of the tray of FIG. 7B.
Figure 7G:
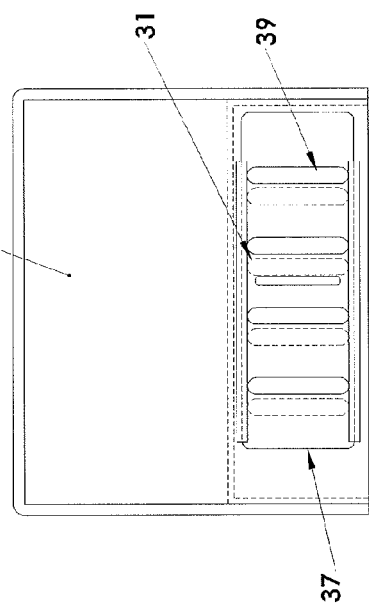
FIG. 7G shows an elevation view of the front face and air regulator of the tray of FIG. 7B.
Figure 7B:
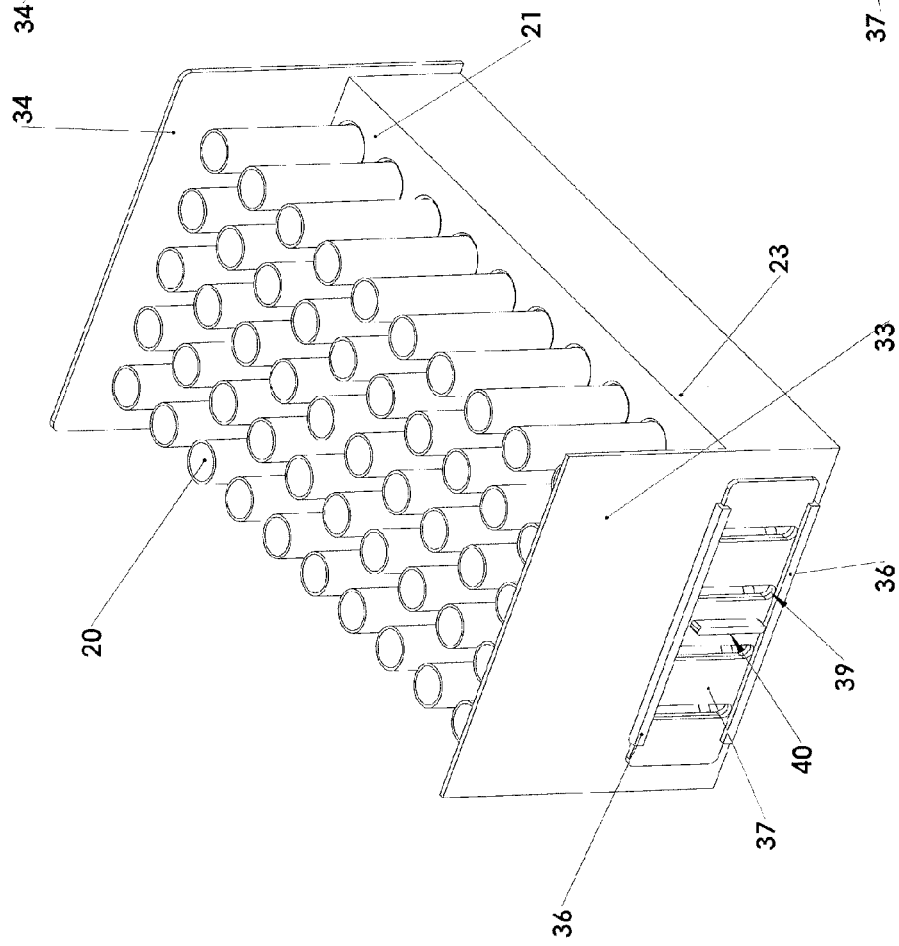
FIG. 7B shows an isometric view of a tray having a vented front and rear faces and air regulators for the tray bin shown in FIG. 7A.
Figure 7C:
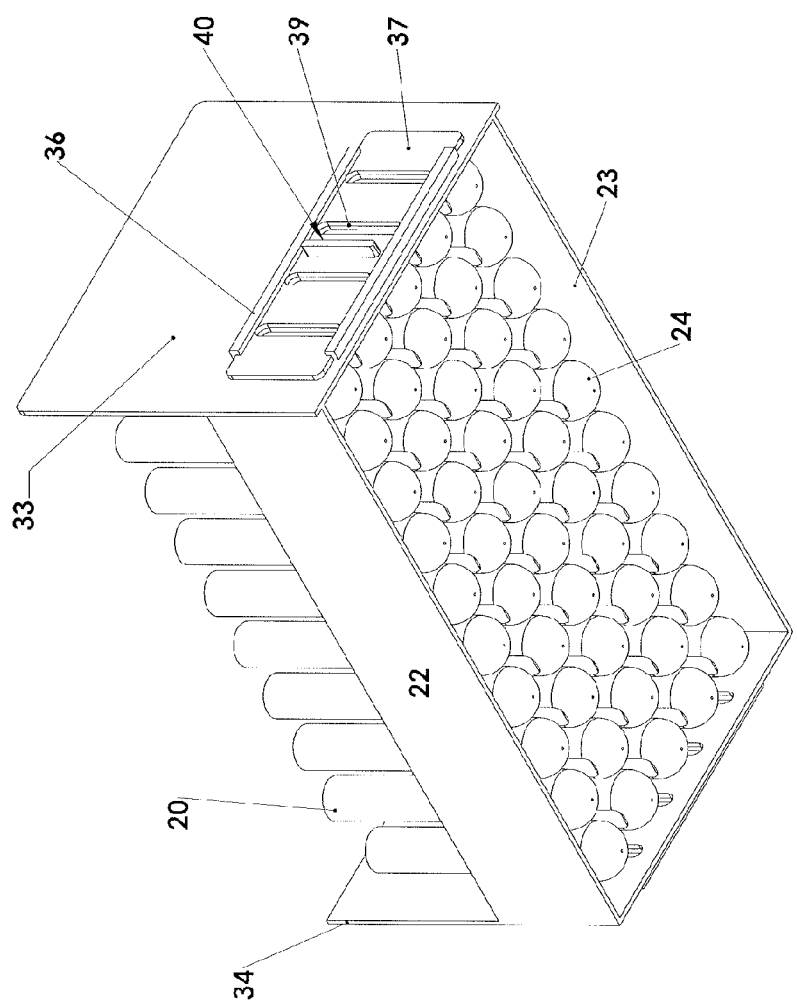
FIG. 7C shows a bottom isometric view of the tray shown in FIG. 7B.
Figure 7D:
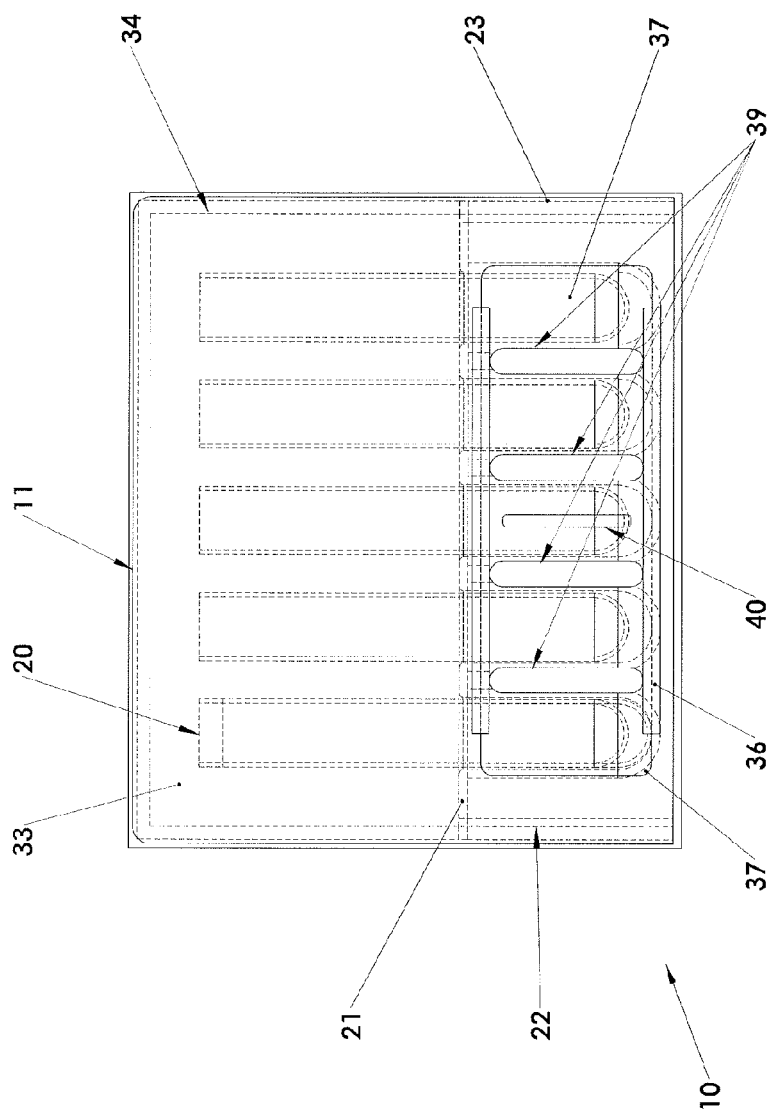
FIG. 7D shows the tray of FIGS. 7B and 7C inserted into and seated in the tray bin of FIG. 7A.
Figure 7E:
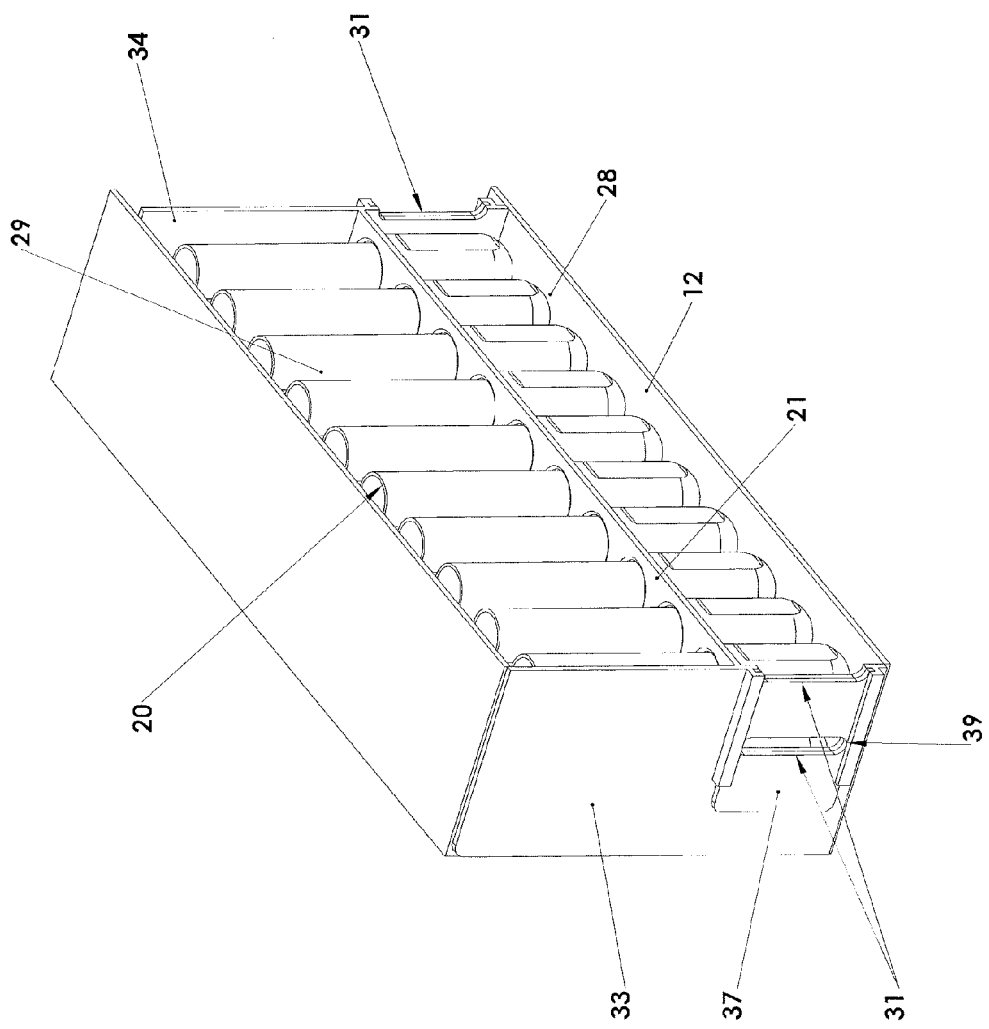
FIG. 7E shows an isometric sectional view of FIG. 7D.

For example, referring to FIG. 7D, the tray front face 33 is seated and sealed against the front opening 16 of the tray bin 10. Thus, when the tray 15 is fully inserted and properly seated within the tray bin 10, the edges of any or all portions of the tray front face 33 that are located above the tray top 21, mate with and overlap the front opening 16 of the tray bin 10 to form a seal or barrier to prevent or minimize the flow of air into the sealed upper compartment 29. All of the edges and surfaces on both the tray front face 33 and the tray rear face 34 that are in contact with or in close proximity to the respective edges and surfaces of portions of the front or rear openings 16 and 32 of the tray bin 10 and that are located above the tray top 21 are adapted to make sufficient contact between themselves to form a seal or barrier capable of eliminating or reducing the air flow between them.

The front and rear faces 33 and 34 can be constructed of material that creates an insulated or thermal barrier between the sealed upper compartment 29 and the environment touching the outer side of rear face 34 and/or the outer side of the front face 33.

Front and rear air registers 37 are slidingly coupled to a pair of tracks 36 that are formed on or mounted to the front and rear faces 33 and 34, immediately above and immediately below the air vent(s) 31 that are also provided in the front and rear faces 33 and 34 of the tray 15. Each air register 37 includes an opening(s) 39 that can be positioned with respect to the air vent(s) 31 to selectively prevent or enable fluid to enter the lower compartment 28 of the tray bin 10. FIG. 7F shows an illustration of a vented rear face 34 in which the opening(s) 39 of the air register 37 are in complete registration with the air vent(s) 31. FIG. 7G shows an illustration of a vented rear face 34 in which the opening(s) 39 of the air register 37 are not in registration with the air vent(s) 31. Those of ordinary skill in the art can appreciate that the air register 37 can be moved between these two limiting positions to introduce a desired controlled temperature and/or humidity into the lower compartment 28 of the tray bin 10. Furthermore, although the figures show that the air vent(s) 31 and openings 39 in the front and rear faces 33 and 34 are identical, the invention is not to be construed as being so limited. For example, the air vent(s) 31 and openings 39 in the front and rear faces 33 and 34 could be manufactured to differ.

Having different size/shape openings 39 and air vents 31 on the front and rear faces 33 and 34 of the tray 15 may be desirable, especially if the tray 15 is to be inserted/removed with a first side facing a first environment, e.g., ambient, while, at a different time, the tray 15 must be inserted/removed with the opposing face facing a second environment, e.g., forced air at a controlled temperature. The first environment can be maintained at a temperature external to the ARSIMS 100, such as the ambient room temperature, or at another temperature specifically controlled and maintained by means other than the ARSIMS 100. The second environment can be a controlled temperature and/or a controlled humidity environment internal to and controlled by the ARSIMS 100. Alternatively, both the first and second environments can be internal to and controlled by the ARSIMS 100, which can control and maintain the two different environments at different temperatures and/or different humidity levels.

To manually adjust the position of the opening(s) 39 of the air register 37 with respect to the air vent(s) 31, a handle 40 can be provided, to allow a user to slide the air register 37 to the right or left. Alternatively, air registers 37 can be adjusted by rotating the air register 37 about an axis; by closing multiple strips such as with a window blind; or by any other mechanisms commonly used to control fluid flow. More preferably, however, the air register 37 is mechanically and automatically positionable by the controller.

Fully closing the air register(s) 37 on the tray rear face 34 while fully or partially opening the air register(s) 37 on the tray front face 33 (FIG. 7E) enables a preponderance or all of the fluid entering the lower compartment 28 to be coming from a first environment, thereby bringing the temperature of the well 24, the tube and/or container 20, and the sample/specimen contained in the tube and/or container 20 to the temperature of the first environment. Conversely, by fully closing the air register(s) 37 on the tray front face 33 while fully or partially opening the air register(s) 37 on the tray rear face 34 enables a preponderance or all of the air entering the lower compartment 28 to be coming from the second environment, thereby bringing the temperature of the well 24, the tube and/or container 20, and the sample/specimen in the tube and/or container 20 to the temperature of the second environment.

Accordingly, by controlling the relative mixture of fluid within the lower compartment 28 of each tray bin 10 from the two environment sources, the controller of the ARSIMS 100 can dynamically create areas or zones having the necessary storage capacity for any given day's workload, over a range of temperature zones that lies in between the absolutes of the two environments. This range can be controlled within 4 to 6 degrees Celsius.

By individually adjusting the amount (area) of the air vent(s) 31 covered or left uncovered by the air register(s) 37 on the tray rear face 34 and/or the tray front face 33, the controller of the ARSIMS 100 can create a desired, temperature- and/or humidity-controlled zone for the samples/specimens stored in a tray 15, within a discrete tray bin 10 or a contiguous group of tray bins 10.

Optionally, a temperature sensing device (not shown) can be disposed in the sealed upper compartment 29 and/or in the lower compartment 28, to provide a feedback loop to the controller for better controlling the temperature in each lower compartment 28.

A further means of preventing or minimizing evaporation of sample/specimen, analyte, diluent, and the like within an open, unsealed, and/or uncapped tube and/or container 20 in a tray 15 is to provide a tray cover. Referring to FIGS. 9A-9G, there are shown various views of a tray cover 80. For illustrative purposes only, the tray cover 80 has a rectangular or rounded rectangular shape; although, any practical shape that can provide an effective seal against the tray top 21 of the tray 15 is acceptable. Indeed, the tray cover opening 85 must be structured and arranged to fit entirely over all of the tubes and/or containers 20 held by the tray 15 and to mate with the tray top 21 in order to form a sealed compartment. More specifically, this involves forming a seal and/or air flow barrier that is capable of eliminating or minimizing the air flow or exchange of air between the sealed compartment and the environment outside of the sealed compartment, e.g., in the tray bin 10, below the tray top 21, and so forth.

The tray cover 80 includes a tray cover top 82, a tray cover front wall 84, a tray cover rear wall 86, and left and right side walls 81 and 83. All or some portion of the tray cover 80 can be made of a material that is transparent, smoked, translucent, light-blocking, solid, and so forth. All or some portion of the tray cover 80 can also be made of material with thermal insulating properties. Advantageously, tray covers 80 are structured and arranged to be stackable inside each other, to minimize the storage space required to store unused tray covers 80.

The tray cover 80 can be manually and/or automatically placed on or removed from a tray 15 while the covered tray 15 is inside the ARSIMS 100. To this end, optionally, the tray cover 80 can be provided with physical features that enable a device, e.g., a robotic arm, a gripper, and the like, to remove or replace the tray cover 80. The tray cover 80 is adapted to mate up with the tray top 21 and the tray 15 in a specific orientation or it may require a plurality of faces or edges to match up in order for the tray 15 and tray cover to properly come together to form a sealed compartment. When a tray cover 80 is properly placed on the tray top 21 it forms a seal or barrier to air flow that eliminates or significantly reduces the air flow able to pass over the tops of the tubes 20 located in the sealed compartment of the tray 15.

Because the tray 15 and tray cover 80 are all that is necessary to form a sealed compartment for handling open or unsealed tubes and/or containers 20, the tray bin 10 used to hold the combined tray 15 and tray cover 80 can be of any size and shape, so long as it is adequate to hold one or a plurality of trays 15 that has/have been covered with a tray cover 80.

Temperature-Controlled Storage Unit, Container Receiving and Removal Area, and Temperature Equilibration Area Having described various embodiments of trays and tray bins, the temperature- and/or humidity-controlled storage unit 50, the container receiving and removal area and the temperature equilibration area 70 of the ARSIMS 100 will now be described.

Referring to FIG. 1, an ARSIMS 100 with a multilevel carousel storage unit 50 is shown. For illustrative purposes, the trays 15 and tray bins 10 are shown having a trapezoidal shape. A trapezoidal-shaped tray and tray bin and/or a pie slice-shaped tray and tray bin maximize the packing density of a circular or arcuate specimen storage carousel 52. Although only a single specimen storage carousel 52 having ten storage levels 42 and 16 tray bins per level is shown, those of ordinary skill in the art can appreciate that there can be more than one carousel 52 (as shown in FIG. 13), the number of levels 42 per carousel 52 can be greater than or less than ten and the number or tray bins per level can be greater than or less than 16. Furthermore, the number of tray bins per level 42 can differ from level to level and the number of levels 42 per carousel 52 can vary from carousel to carousel.

Preferably, each carousel 52 in the multilevel carousel storage unit is enclosed within an insulated housing 55 having an insulated outer (or inner) skin 51 to insulate the inner workings of the ARSIMS 100 from the laboratory in which it is disposed. The inner portion of the insulated housing 55 can be adapted to provide a second environment 59, e.g., an ambient environment. A first environment 58 that is temperature and humidity controllable can be provided within an inner (center) portion 57 of the sample carousel 52. For example, the sample carousel 52 can be structured and arranged to force controlled-temperature and/or controlled-humidity air flow from the center portion 57 of the sample carousel 52 radially into at least one tray bin 10. Advantageously, the air flow into each tray bin 10 on each level 42 as well as the air flow into each level 42 in the sample carousel 52 can be controlled and adapted so that discrete, controlled temperature zones can be created for storing samples/specimens that require storage at a discrete temperature according to the processing phase, the sample/specimen, and the next test.

The sample carousel 52 can be adapted to rotate in a unidirectional manner, e.g., clockwise or counter-clockwise, or in a bi-directional manner. Rotation of the sample carousel 52 is necessary to move a specific tray bin to a loading/unloading position 65.

Although the rear walls 17 of the tray bins 10 shown in FIG. 1 are solid, this is done for illustrative purposes only. Those of ordinary skill in the art could include any of the tray bin rear walls that were described hereinabove. A solid rear wall 17 will prevent air flow into the lower compartments 28 of fully-inserted and properly-seated trays 15. Alternatively, the carousels 52 could include vented rear walls 38 with one or more air vents 31 (with or without air registers 37) and/or rear openings 32. Each level 42 can include tray bins 10 having a combination of two or more rear walls or a specific level(s) 42 can be dedicated to just solid rear walls 17, just vented rear walls 38, just rear openings 32, and so forth.

The ARSIMS 100 also includes a container receiving and removal area 60 and a temperature equilibration area (TEA) 70. The TEA 70 is a separate temperature-controlled area in which samples/specimens at one temperature are placed so that they can equilibrate to another temperature before further processing or testing. TEAs 70 allow samples/specimens, before they are placed on the track, to be brought from the temperature at which they were stored within the storage unit 50 to the temperature the analyzer is expecting the samples/specimens to be when they arrive for analysis. In addition to separate TEAs 70, the warm up and/or cool down of tubes and/or containers 20 and samples/specimens can be accomplished within a tray bin 10 by bringing the temperature, at a controlled rate, from a first temperature, e.g., refrigerated, to a second temperature, e.g., ambient.

The container receiving and removal area 60 can include a track loading area 61 and a track unloading and disposal area 62. A plurality of robotic arms 63 are provided in the container receiving and removal area 60. The robotic arms 63 are adapted to transport a single tube and/or container 20 and/or one or more trays 15. For example, a first robotic arm 63a can be structured and arranged to insert individual tubes and/or containers 20 into the wells 24 of a tray 15.

A second robotic arm 63b can be structured and arranged to pick up an entire tray 15 from the track loading area 61 and to insert it into, for example, the front opening 16 of an open tray bin 10 in the sample carousel 52 or the temperature equilibration area (TEA) 70. The second robotic arm 63b can be further adapted to remove trays 15 from a tray bin 10 and to reinsert the removed tray 15 into another tray bin 10 or to place the removed tray 15 on the track unloading and disposal area 62.

The second robotic arm 63b shown in FIG. 1 is mounted on a movable axle 64 that is translatable to move the robotic arm 63b from proximate the track loading area to the loading/unloading position 65 of the sample carousel 52. The second robotic arm 63b is further adapted to travel up and down the axle 64 to access any level 42 of the sample carousel 52 and/or the TEA 70.

A third robotic arm 63c can be provided at the track unloading and disposal area 62 for the purpose of removing individual tubes and/or containers 20 from a tray 15 and disposing of the removed tubes and/or containers 20. Disposal can include placing the removed tubes and/or containers 20 into one or more bio-hazard waste containers 68, e.g., via an opening 66 in the top surface of the track unloading and disposal area 62 or into sample holding area 67. Notwithstanding the advantages of robotic arms 63, the tubes and/or containers 20 and the trays 15 can also be installed and removed manually by laboratory personnel.

Although not shown in FIG. 1, the ARSIMS 100 also includes a device for reading a bar code and/or RFID tag that is attached to each tube and/or container 20 or other indicia of the sample/specimen contained in the tube and/or container 20 as soon as the sample/specimen and tube and/or container 20 are loaded into, or presented to, the ARSIMS 100 by any means. Accordingly, the ARSIMS 100 is capable of determining the location of the coded tube and/or container 20 as well as, and more importantly, the sample/specimen contained therein at any point in time and further determining where it should be stored within the system before its next processing phase. The bar code reader(s) and/or RFID reader associated with checking in a new sample/specimen in a tube and/or container 20 can be integrated into the ARSIMS 100 or can be an external, stand-alone device. If external, the reader can be coupled to the ARSIMS 100 using at least one of a hardwire, a fiber optic cable a wireless connection, and so forth.

Also not shown in FIG. 1 is an optional vision-based subsystem that can be used to determine, for example, whether or not a tube and/or container 20 is sealed, unsealed, capped, uncapped, covered or uncovered; whether or not the tube and/or container 20 has been spun; whether or not the sample/specimen contained in the tube and/or container 20 is lipimic, icteric, and/or hemolyzed; the quantity of useable sample/specimen remaining in the tube and/or container 20; the color of the top of the tube and/or container 20; and so forth.

Although the multilevel carousel ARSIMS 100 has been described with the tray bin loading/unloading occurring at the outer diameter of the sample carousel 52 and temperature control being provided at the inner diameter of the sample carousel 52, the multilevel carousel ARSIMS 100 could also be configured so that tray bin loading/unloading occurs at the inner diameter of the sample carousel 52 and temperature control is provided at the outer diameter of the sample carousel 52.

Figure 2:
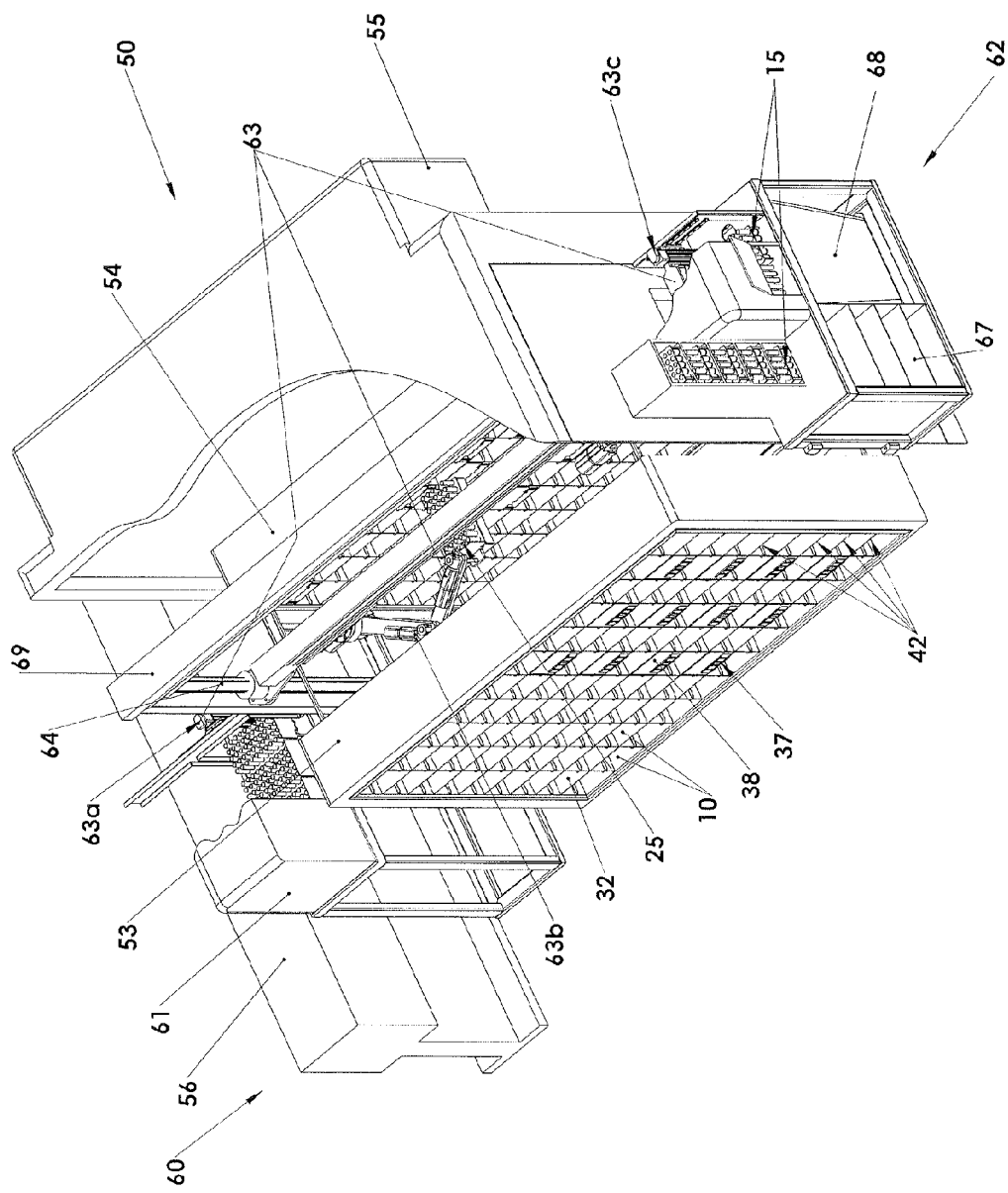
FIG. 2 shows an automated, refrigerated specimen inventory management system having dual shelving specimen storage in accordance with the present invention.
Figure 6:
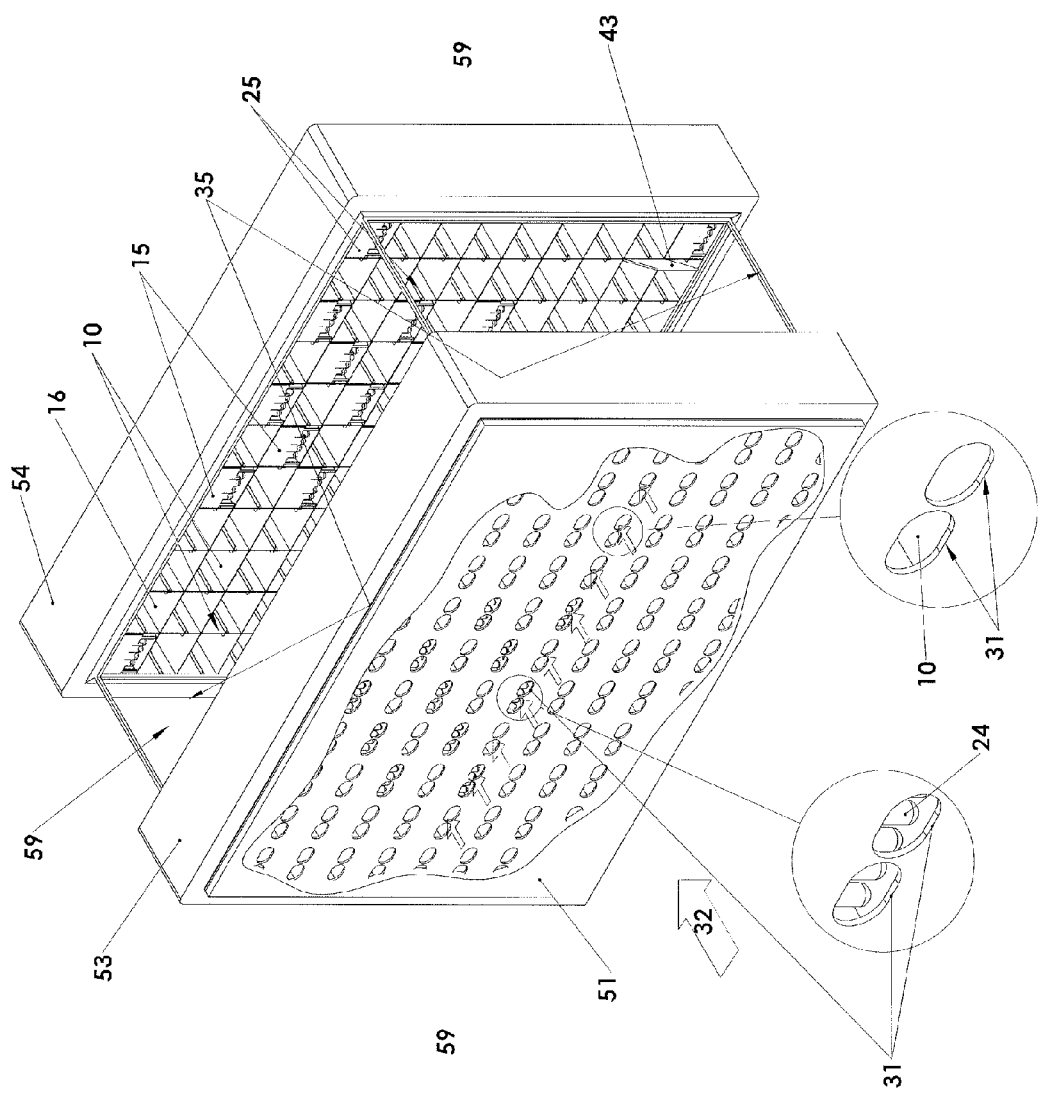
FIG. 6 shows an automated, refrigerated specimen inventory management system having rear-vented, dual shelving storage in accordance with the present invention.
Figure 8:
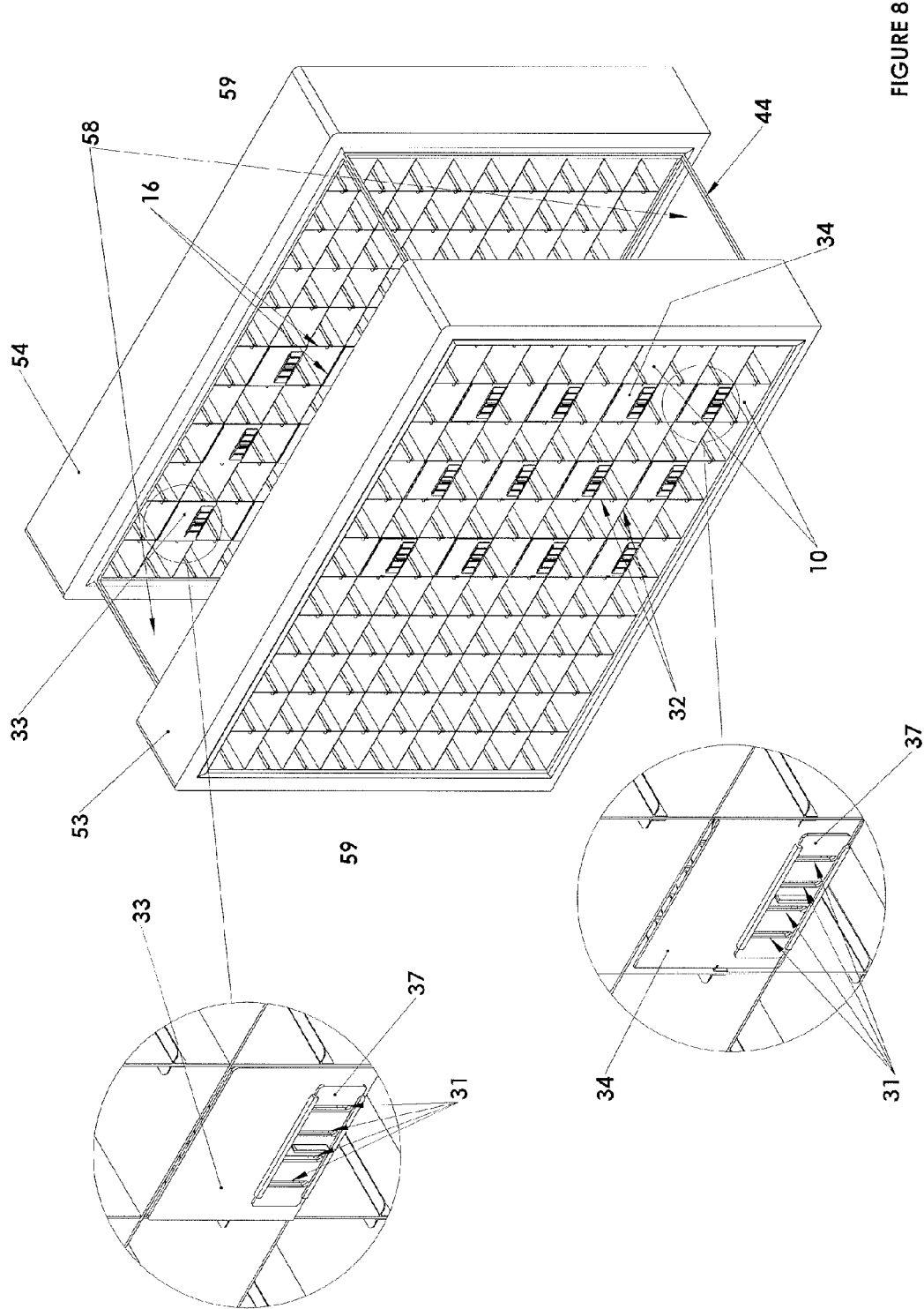
FIG. 8 shows an automated, refrigerated specimen inventory management system having dual shelving storage with open tray bins for trays with vented front and rear faces and air regulators in accordance with the present invention.
Figure 9A:
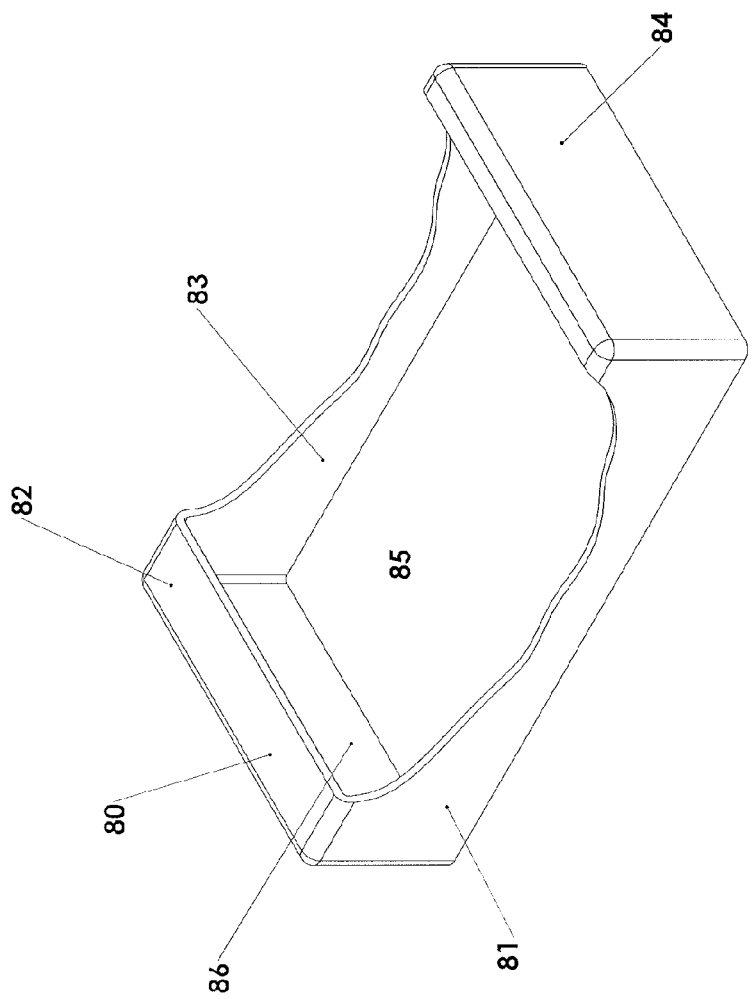
FIG. 9A shows an isometric view of a tray cover for covering a tray.
Figure 9C:
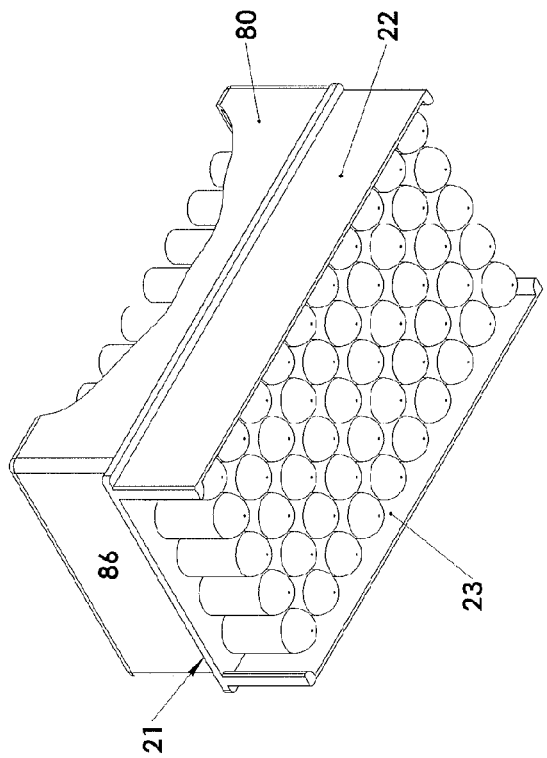
FIG. 9C shows a bottom isometric view of a tray with a tray cover.
Figure 9B:
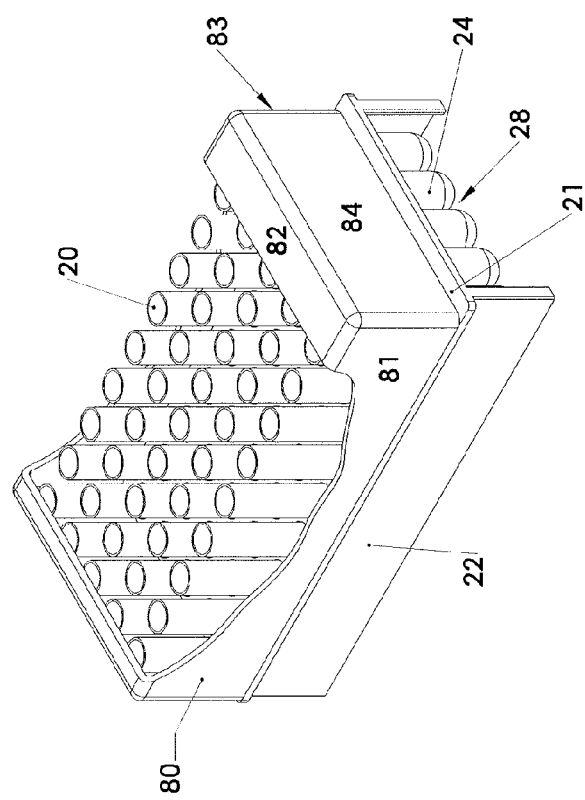
FIG. 9B shows an isometric view of a tray with a tray cover.
Figure 9E:
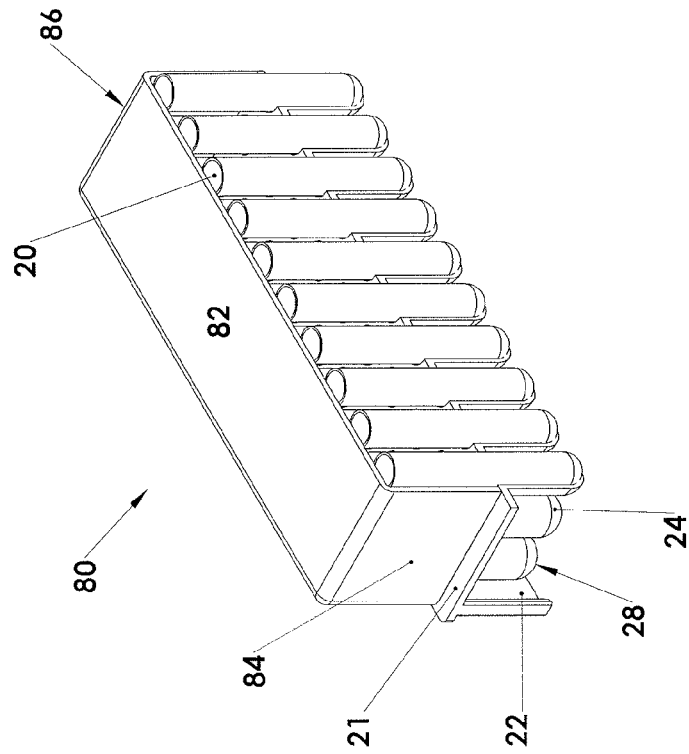
FIG. 9E shows an isometric sectional view of FIG. 9D.
Figure 9D:
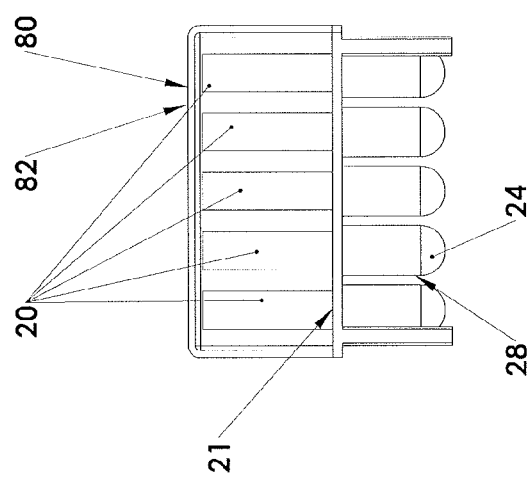
FIG. 9D shows an elevation view of the covered tray of FIGS. 9B and 9C.
Figure 9G:
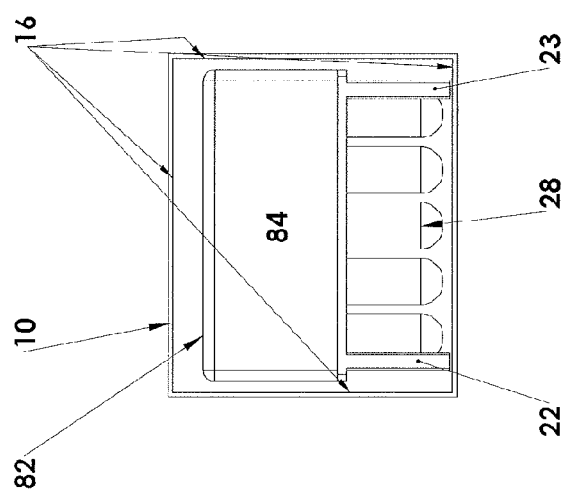
FIG. 9G shows an elevation view of the covered tray of FIGS. 9B and 9C inserted into and seated in a tray bin without tray slides.
Figure 9F:
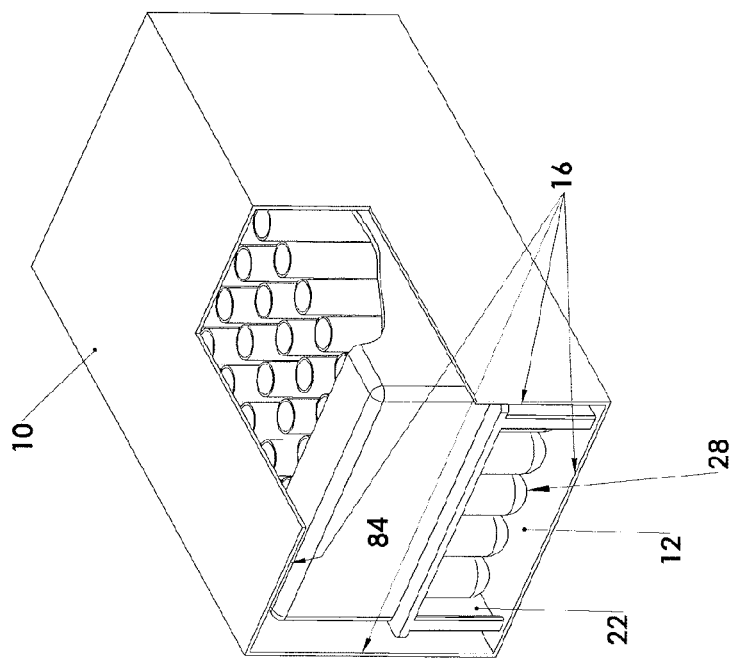
FIG. 9F shows an isometric view of the covered tray of FIGS. 9B and 9C inserted into and seated in a tray bin without tray slides.

Referring to FIGS. 2, 4, 6, and 8, a dual shelving sample storage unit 50 for an ARSIMS 100 is shown. The components of the dual shelving sample storage ARSIMS 100 are essentially the same as those described hereinabove in connection with the multilevel carousel storage unit 50 except that the sample carousel 52 has been replaced by a pair of shelves 53 and 54, each shelf 53, 54 having a plurality of tray bins 10. More specifically, FIG. 2 shows tray bins 10 with rear openings 17 (FIG. 7A) and corresponding vented front and rear wall trays 10 as described in connection with FIGS. 7B-7G, optionally including air registers 37. FIG. 4 shows the same as FIG. 2 except that an insulated cover 51 is provided and an optional tray bin door 43 can be included in conjunction with some or all of the tray bins 10. FIG. 6 shows tray bins 10 having vented rear walls 38 (FIG. 5A) and corresponding trays 15 as described in connection with FIGS. 5B-5D. FIG. 8 shows tray bins 10 with rear openings 32 (FIG. 7A) and corresponding trays 15 as described in connection with FIGS. 7B-7G that include air registers 37.

At least one second robotic arm 63b, axle 64, and an optional gantry 67 can be disposed between the pair of shelves 53 and 54 for inserting and removing trays 15 into of from tray bins 10. The front openings 16 of the tray bins 10 for each shelf 53 and 54 are closest to the second robotic arm 63b and its surrounding environment while the rear walls 17 or 38 or rear openings 32 of the tray bins 10 are adjacent to the second environment 59 or are encased within an insulated skin 51. Hence, the front openings 16 of each tray bin 10 face each other. Each of the shelving units 53, 54 can be entirely contained within an insulted skin 51, all or any part of which can be maintained at a controlled temperature.

The number of tray bins 10 in each level 42 and the number of levels in each shelf 53 and 54 shown in the figures are illustrative. Indeed, the number of tray bins 10 in each level 42 and the number of levels in each shelf 53 and 54 can vary.

Although FIGS. 2, 4, 6, and 8 suggest dual shelving ARSIMS 100 in which trays 15 are loaded from the area between the opposing shelves 53, 54, that is done for illustrative purposes only. In other embodiments, trays 15 can be loaded into tray bins 10 from the shelf side facing away from the space between the shelving units 53, 54 or from both sides of the shelves 53, 54.

FIG. 4 shows tray bins 10 having doors 43, which is an optional feature. Tray bin doors 43 can be used to close off, e.g., by sliding up and down, by sliding left and right, by rotating about a fixed axis, and so forth, either the front opening 16 of a discrete tray bin 10 (as shown in FIG. 4), and/or the rear opening 32 of a discrete tray bin 10. Tray bin doors 43 are structured and arranged to be opened or closed manually or automatically, which can include by using a robotic arm 63c. Although FIG. 4 shows a tray bin door 43 that covers the entire front opening 16, alternatively, the tray bin door 43 can only cover the area below the level of the tray top 21 and/or can include air vents 31 and/or air registers 37 similar to the air vents and air registers described in connection with FIG. 7B, et seq.

Preferably, when closed, the tray bin door 43 helps to maintain a sealed upper compartment 29 that eliminates or reduces the air flow between the tray bin door 43 and the front opening 16 or rear opening 32 of the tray bin 10 with which it is paired. Only the portion of the tray bin door 43 above the level of the tray top 21 must be made of a material that prevents or minimizes the flow of air through that portion of the tray bin door 43. The tray bin door 43 can be made of an insulating material.

Optionally, a single tray bin door 43 can be structured and arranged to cover a plurality of tray bins 10 and/or any other type of enclosed volume capable of holding one or a plurality of trays 15 of any size or shape.

Also shown in FIG. 4 is a frame 44 that is provided between the two shelves 53 and 54 to provide lateral support and to maintain the shelves 53 and 54 at a fixed distance from each other.

As shown in FIG. 6, the second environment 59, e.g., ambient room temperature, completely surrounds the insulated exterior portion (skin) 51 of the dual shelves 53, 54 while a temperature-controlled first environment is provided between the insulated outer skin 51 and the vented rear walls 38 or rear openings 32 of the tray bins 10. Pressurized air 41 at a controlled temperature and/or humidity can be forced into the lower compartments of the tray bins 10 through the air vents 31 (See Detail A and B of FIG. 6), which are located on the vented rear walls 38 of the tray bin 10. The temperature-controlled forced air 41 circulates through the lower compartment 28, cooling the samples/specimens in the tubes and/or containers 20 by convection, before exiting the lower compartment 28 via the portion of the front opening 16 of the tray bin 10 that is below the level of the tray top 21. The exhausted air 35 is introduced into the space between the dual shelving units 53 and 54 where a return air duct (not shown) can cool it, heat it, filter it, and the like before re-circulating it again to the rear walls 38 or rear openings 32 of the tray bins 10. Although FIG. 6 has been described with the temperature-controlled forced air traveling form the vented rear walls 38 or rear openings 32 of the tray bins 10 towards the front openings 16 of the tray bins 10, those of ordinary skill in the art can appreciate that the temperature-controlled forced air could just as easily be delivered from the front openings 16 towards the vented rear walls 38 or rear openings 32.

Advantageously, all or any subset of tray bins 10 can be coupled to a dedicated air duct (not shown) that is adapted to deliver forced air at a discrete temperature that is tailored for the corresponding tray and the samples/specimens stored in that tray 15. Circulating air, at defined temperatures and humidity, can also be delivered to an individual tray bin 10 or group(s) of tray bins 10. In short, one shelf 33, 34 or portion of one shelf 33, 34 can be cooled to a first temperature by a first fluid stream and another shelf 33, 34 or portion of the same shelf 33, 34 can be cooled to a second, different temperature by a second fluid stream. The delivered fluid streams can differ in temperature, humidity, pressure, and so forth or, alternatively, the amount of delivered fluid that is allowed to enter and circulate through the lower chamber 28 can be controlled, to provide different temperatures in the different shelves 33, 34 or portions of the same shelf 33, 34.

Optionally, tray bin doors 43 can be added to FIG. 6 to seal or create a barrier to air flow by mating with the front opening 16 and/or rear opening 32 of a tray bin 10 to help create a sealed upper compartment 29. Air registers 37 can also be added to manually and/or automatically control air flow through the air vents 31.

FIG. 8 shows an illustrative dual shelving ARSIMS 100 having a plurality of the tray bins 10 with rear openings 32 and trays 15 described hereinabove in connection with FIG. 7A-7E. In the illustrative embodiment shown in FIG. 8, a first, temperature-controlled environment 58 is provided in the space between the two shelves 53 and 54 and a second environment (ambient) 59 is provided on the opposite sides of the shelves 53 and 54. According to the illustrative embodiment, the front openings 16 of the tray bins 10 for each shelf 53, 54 and the vented front face 33 of the fully-inserted and properly-seated trays are adjacent to the first environment 58 while the rear openings 32 of the tray bins 10 for each shelf 53, 54 and the vented rear faces 34 of the fully-inserted and properly-seated trays 15 are adjacent to the second environment 59. Those of ordinary skill in the art can appreciate that the environments 58 and 59 could be switched and that the locations of the vented front and rear faces 33 and 34 of the trays 15 with respect to the environments 58 and 59 can differ from that shown.

Access to the rear air vents 37 and associated air register 37 can be through vents or cut-outs in the outer skin (not shown) and/or via air ducts (not shown). Alternatively, a separate insulated outer skin may not be necessary as the vented rear faces 34 themselves can be manufactured of an insulated material to form all or a portion of the outer skin.

Optionally, the front 16 or rear opening 32 of the tray bin 10 can include a tray bin door 43. Air registers can also be added to manually and/or automatically control air flow through the air vents 31. Although FIG. 8 has been described for use in connection with tray bins 10 and trays 15 shown in FIGS. 7A-7E, the ARSIMS 100 can also include tray bins 10 and trays 15 such as those shown in FIG. 3A, et seq. and FIG. 5A, et seq.

Figure 11:
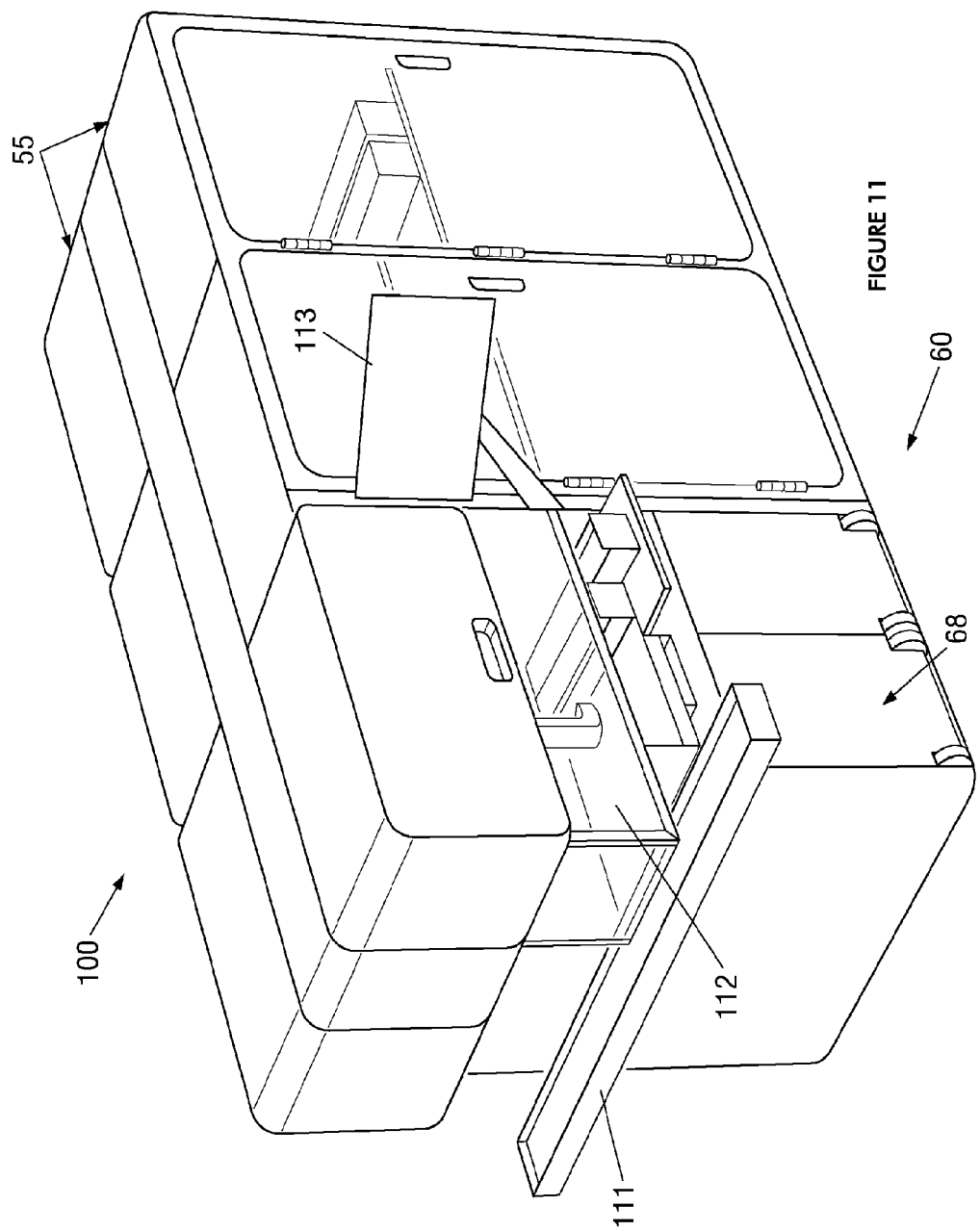
FIG. 11 shows an isometric view of the storage unit shown in FIG. 10 that has been enclosed in an insulated outer skin.

FIG. 10 and FIG. 11 show another alternate dual shelving storage unit and said alternate dual shelving storage unit encased within an insulated housing 55, respectively. FIG. 11 shows a container receiving and disposal area 68. Trays 15 arrive at the container receiving and disposal area 60 of the ARSIMS 100 via a track 111. A robotic arm 112 or other handling device removes the tray(s) 15 from the track 111. If the tubes and/or containers 20 stored in the tray(s) 15 are ready for disposal, the tubes and/or containers 20 and/or the entire tray(s) 15 can be deposited in waste bins 68 for biohazardous waste materials. If the tubes and/or containers 20 require further processing and need to be stored at a specific temperature for a specific amount of time, the robotic arm 112 will introduce the tray(s) 15 into the ARSIMS 110 where the tray(s) 15 will be placed in the TEA 70 and/or into a discrete tray bin 10 whose temperature and humidity can be controlled. The container receiving and disposal area 60 can also provide an operator interface which can include an input/output device 113 such as a touch-screen monitor.

The dual shelving storage unit shown in FIG. 10 differs from previously shown and described storage units in that tray bins 10 have a larger, open area that makes it easier to fully insert and properly seat a plurality of trays 15 into a tray bin 10 at one time. Although the tray bins 10 in FIG. 10 are capable of storing five trays 15 this is done for illustrative purposes only.

Figure 12E:
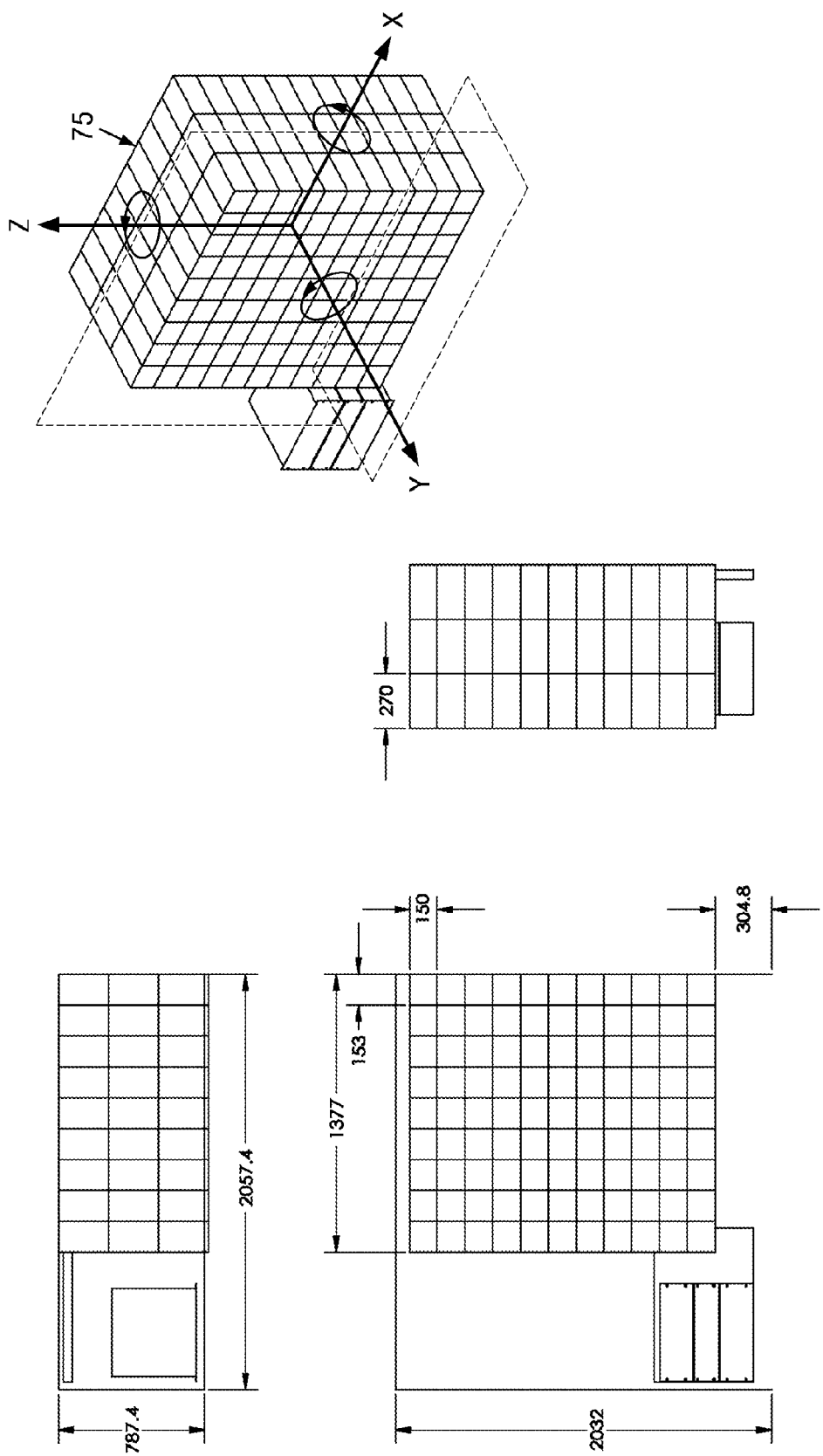
FIG. 12E shows plan, isometric, and elevation views of a shuffle-type storage unit.

FIGS. 12A-12G provide additional, non-exclusive embodiments for temperature controlled storage units 50 of the ARSISM 100. An arc concept (FIG. 12A) is a modification to the multilevel sample carousel unit described hereinabove in connection with FIG. 1. Although FIG. 12A shows that each level 42 is capable of holding eight trays 15, that is done for illustrative purposes only. Furthermore, although FIG. 12A shows that the trays 15 are uncovered and the tray bins 10 are open, those of ordinary skill in the art can appreciate that tray covers 80 can be employed to prevent or minimize evaporation from the tubes and/or containers 20.

FIG. 12B shows a peg board temperature-controlled storage unit in which individual capped, sealed, and/or closed tubes and/or containers 20 are inserted into an opening 87 in the "peg board" 91. One or more peg boards can be cantilevered from upper and lower rods 88, which are supported by a frame 89. Preferably, the peg boards 91 are slidable along the upper and lower rods 88.

Figure 12F:
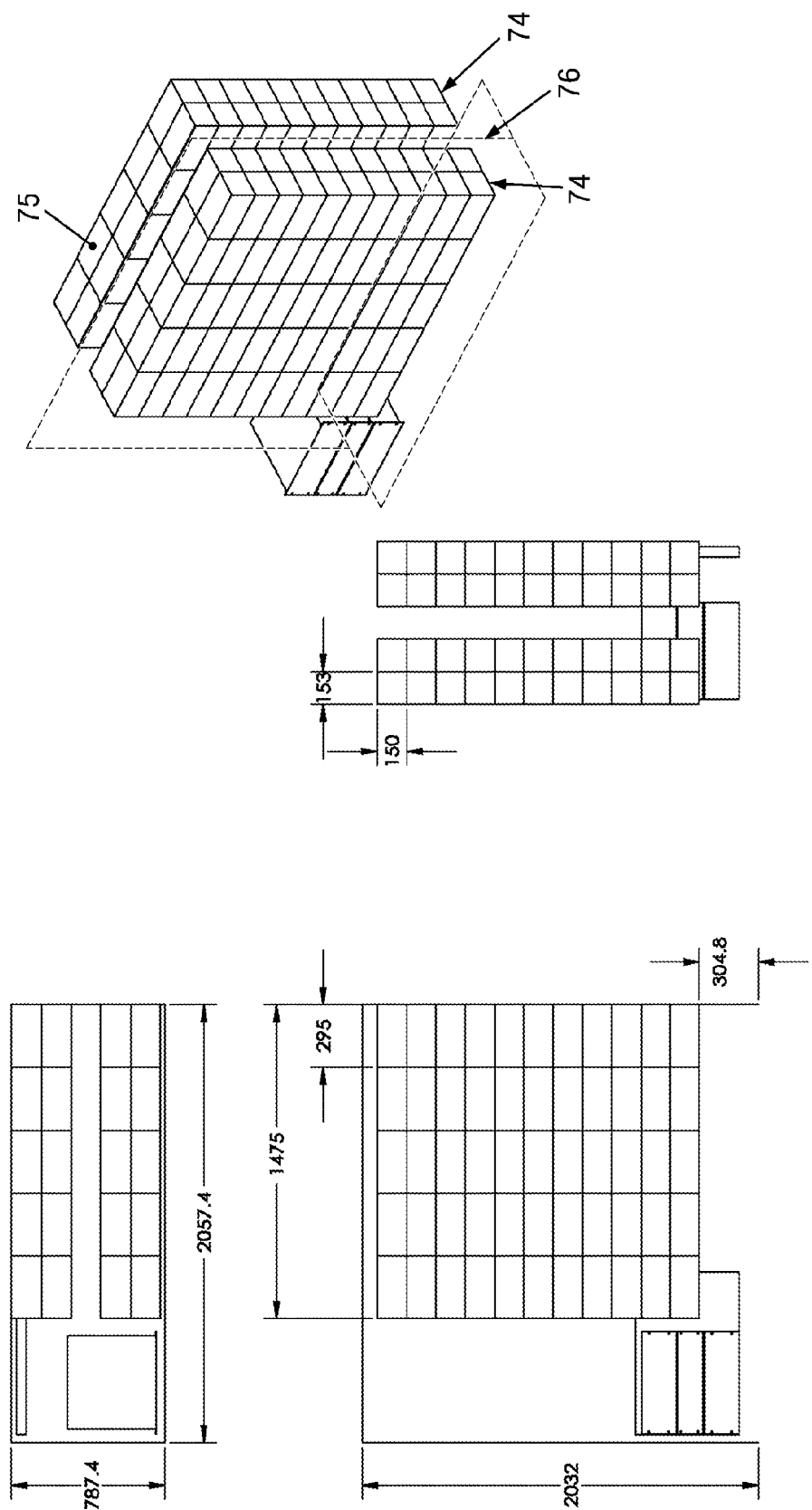
FIG. 12F shows plan, isometric, and elevation views of a movable bookcase-type storage unit.
Figure 12G:
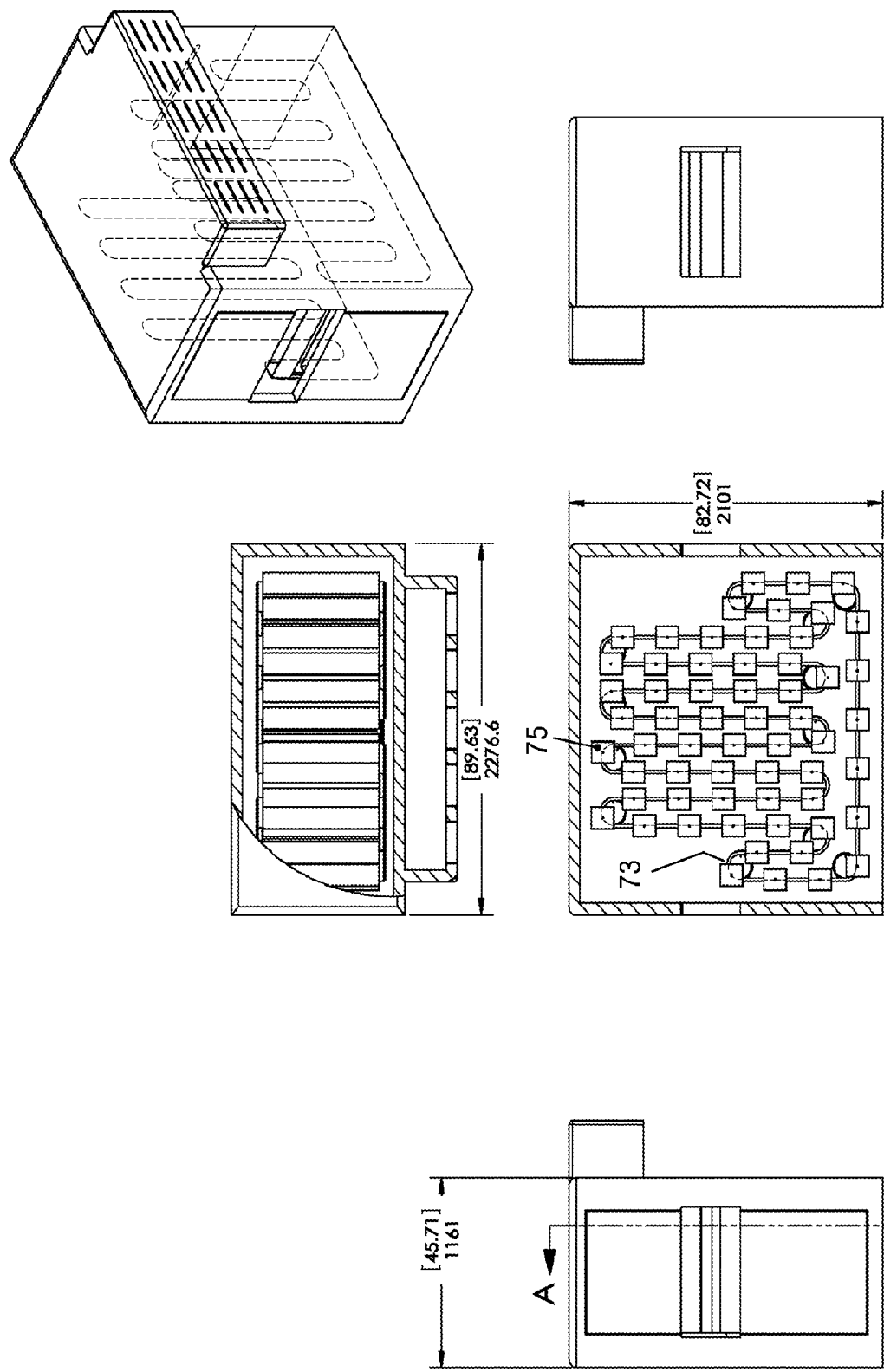
FIG. 12G shows plan, isometric, and elevation views of a serpentine-type storage unit.

FIGS. 12C and 12D show dual and single Ferris wheel temperature-controlled storage units that include a plurality of tray bins 75 that are operationally coupled to a closed, rotatable track 73 of a first 71 or a second "Ferris wheel" 72. FIG. 12G shows a serpentine controlled storage unit that also include a plurality of tray bins 75 that are operationally coupled to a closed, rotatable track 73 that travels along a serpentine path rather than a circular or oval path as with the Ferris wheel concepts.

FIG. 12E shows a temperature- and humidity-controlled storage unit that uses a shuffle concept. FIG. 12F shows a temperature- and humidity-controlled storage unit that uses a movable bookcase concept. The shuffle concept provides a plurality of tray bins 75 that can be structured and arranged to be rotatable about three orthogonal axes, much like a Rubik's cube. The movable bookcase concept includes a plurality of stacks 74 that include a plurality of tray bins 75. The stacks are translatable in orthogonal directions within a plane such that an open space 76 is always provided between two of the stacks 74.

A larger version of the movable bookcase concept is shown in FIGS. 16 and 17. This version includes single stacks 74 that move individually and back-to-back stacks 77 that move as a unit. Open spaces 76 can be provided between stacks of interest 74 and 77. Preferably, a rotating robotic arm or picker (not shown) is structured and arranged to enter an open space 76, to translate therein, and to elevate to any desired tray bin 75, to deposit or withdraw a tray 15 from a tray bin 10. Each stack 74, 77 can include a separate, dedicated motor means by which the stack 74, 77 can be moved. Motor means can include, for example and not for the purpose of limitation, wheels or a belt/track system.

Referring to FIGS. 14A and 14B, a multilevel, shuttle storage unit will be described. FIG. 14A shows a single active shelf 42 and FIG. 14B shows a plurality of levels 42 and an elevator/dumb waiter 99 that is structured and arranged to transport trays 15 between levels 42.

Each level 42 includes a plurality of conveying surfaces 94, e.g., conveying belts, that is adapted to transport trays 15 to any desired location on the level 42. The number of trays 15 that can be stored on each level 42 can vary. At least one space 96 is a pick-up/deposit point for the elevator/dumb waiter 99. Alternatively or additionally, a robotic arm (not shown) can be provided at the pick-up/deposit point 96.

Bidirectional movement in two dimensions can be provided by any means known to the art. FIGS. 14A and 14B use conveyor belts 94 to translate in two dimensions. Teeth, gears, wheels, sprockets, and the like can be added to the belt 94 for engaging one of the outer walls of a plurality of trays 15 or for engaging a corresponding part to the teeth, gears, sprockets, and the like.

FIG. 15 shows an ARSIMS 100 having split storage, which allows laboratory personnel to separate the functions of specimen storage between at least two storage modules 101, 102. The first storage module 101, which includes an operator interface for interfacing with the ARSIMS 100, provides "local" storage for trays 15 and individual tubes and/or containers 20 that will be processed in the near term; whereas, a second storage module 101 can provide "remote", longer-term storage for trays 15 and individual tubes and/or containers 20 that will not be processed until later. The second storage module 102 shown in FIG. 15 can employ any of the storage units described hereinabove or a combination thereof.

The first and second storage modules 101 and 102 are coupled by a plurality of transportation conduits 103 and 104 that are structured and arranged to deliver trays 15 from the first storage module 101 to the second storage module 102 and vice versa. The means of transportation can be by conveyor belts, pneumatically, and so forth. Once a tray 15 arrives at the second storage module 102, a robotic arm, elevator, and the like (not shown) is adapted to remove the tray 15 from the transportation conduit 103 and insert the tray 15 into a discrete, pre-determined tray bin 10. Preferably, the robotic arm, elevator, and the like are adapted to translate laterally and to move in an up and down direction.

At the operator interface at the first storage module 101 there are provided a plurality of input/output recesses. For example, trays 15 containing a plurality of tubes and/or containers 20 can be loaded into the first storage module via a loading port 106 and unloaded from the first storage module 101 via an unloading port 107. In addition to having a loading port 106 for an entire tray 15 or multiple trays 15, the operator interface also includes an input port 105 for a single tube and/or container 20. Once the individual tube and/or container 20 is inserted into the first storage module 101, it can automatically be inserted into a tray containing like tubes and/or containers 20, e.g., using a robotic arm and the like.

At least one waste bin 108 for bio-hazardous waste material is provided proximate the unloading port 107 for quick and safe disposal of completed and/or expired samples/specimens and tubes and/or containers 20.

Other embodiments of the main temperature- and humidity-controlled storage unit of this invention can include any or a combination of the storage units and storage concepts mentioned hereinabove.

Controller

The controller to the ARSMIS 100 is structured and arranged to control the movement, location, and temperature of each of the plurality of tubes and/or containers 20 and trays 15 as well as to control the temperature and/or humidity of the environment in and/or around a plurality of containers (tray bins) 10 for holding the plurality of tubes and/or containers 20 and trays 15. For this purpose, the controller uses a schedule that identifies and tracks each sample/specimen contained in a tube and/or container 20, the testing to be performed on each sample/specimen, and the desired and/or preferred temperature of the sample/specimen when it is presented and introduced into an analyzer.

The controller can be implemented using a processor, microprocessor, personal computer, and the like having an input/output interface(s) and adequate memory, e.g., volatile random access memory (RAM) and non-volatile read-only memory (ROM). The controller ROM, which could include all or some portion of the data storage, can include software or hardware that includes applications, algorithms, driver programs, and the like for operating the track 113, the temperature-controlled storage unit(s) 50, the TEA 70, the specimen receiving and disposal area 60, the robotic arms 63, and the various other subsystems. Any program executed on the controller's RAM is adapted to selectively call and execute any called driver programs, application, algorithm, and the like stored in the controller ROM.

Advantageously, the controller is adapted to dynamically reconfigure, i.e., increase or decrease, the amount (volume) of storage space available for each desired temperature zone, to accommodate current, real-time sample/specimen storage requirements. A temperature zone can relate to at least one of an enclosed area, a tray bin 10, and the like. Each zone can be maintained at a unique temperature/humidity setting or multiple zones can be set to the same temperature/humidity setting at the same time.

A further advantage of the invention is that a user can define the period of time a sample/specimen remains on the system before it is automatically discarded. A unique period of time for storing a discrete sample/specimen can be established based on, for example, the type of sample, draw/collection site, draw/collection date/time, requesting doctor, test(s) performed on the sample/specimen, time the sample/specimen was first placed into the ARSIMS 100, and so forth. Preferably, the ARSIMS 100 automatically disposes of the tube and/or container 20 in which the sample/specimen is stored when the designated storage time has elapsed based on the criteria applicable to each sample/specimen into a biohazard waste container 68.

Many changes in the details, materials, and arrangement of parts and steps, herein described and illustrated, can be made by those skilled in the art in light of teachings contained hereinabove. Accordingly, it will be understood that the following claims are not to be limited to the embodiments disclosed herein and can include practices other than those specifically described, and are to be interpreted as broadly as allowed under the law.

What we claim is:

1. A specimen inventory management system for holding a plurality of containers containing a sample under test in at least one of a pre-analytical phase, an in-process phase, and a post-analytical phase of processing at a storage temperature appropriate for the sample under test and the phase of processing, the system comprising:
   a source configured to provide a cooling or warming fluid having a controlled temperature to selective locations;
   at least one area having a plurality of temperature zones, each zone of said plurality of temperature zones being structured and arranged to hold a discrete number of the plurality of containers at a desired controlled temperature and/or controlled humidity, wherein the source selectively provides the cooling or warming fluid to the plurality of temperature zones, and wherein the desired controlled temperature and/or controlled humidity is controlled at least in part by selectively restricting flow of the cooling or warming fluid into each individual container in the discrete number of the plurality of containers;
   a container receiving and removal area configured to receive each of the plurality of containers and to insert said each of the plurality of containers in one of the plurality of temperatures zones, and to remove said each of the plurality of containers from a respective temperature zone for disposal or for analysis;
   a temperature equilibration area adapted to enable containers to reach a temperature equilibrium commensurate with a temperature at a next destination; and
   a controller configured to identify the storage location and storage temperature of each of the plurality of containers,
   wherein at least one of the plurality of temperature zones includes at least one tray bin portion and corresponding removable tray portion that is adapted to be inserted into and removed from the at least one tray bin portion,
   wherein each tray portion is structured and arranged to include:
      a tray to portion having a plurality of openings configured to retain the plurality of containers, the tray to portion providing a substantially airtight seal with the tray bin portion when fully inserted within and properly seated in said tray bin portion; a pair of side wall portions, which are attached to the tray top portion;
      one of an open front end portion, a partially open front end portion, and a closed front end portion; and
      one of an open rear end portion, a partially open rear end portion, and a closed rear end portion.

2. The system as recited in claim 1, further comprising a plurality of temperature sensing devices that are disposed in the temperature zones and adapted to provide temperature data to the controller.

3. The system as recited in claim 1, further comprising a container disposal device configured to dispose of discrete containers containing samples under test whose maximum storage time has been reached.

4. The system as recited in claim 1, wherein the storage temperature appropriate for a first sample under test or a first phase of processing differs from the storage temperature appropriate for a second sample under test or a second phase of processing within the plurality of containers.

5. The system as recited in claim 1, further comprising a code reading device that is adapted to read sample-identifying code that is provided on or attached to each of the plurality of containers, to a group of containers or to a tray of containers at a discrete location and to provide at least one of the sample-identifying code and the discrete location of each of the plurality of containers, the group of containers, or the tray of containers to the controller.

6. The system as recited in claim 5, wherein the controller is adapted to identify at least one of the storage location and the storage temperature of each of the plurality of containers, the group of containers, or the tray of containers based on the sample-identifying code, the phase of processing, and an analysis protocol for said sample-identifying code.

7. The system as recited in claim 1, wherein the controller is adapted to dynamically reconfigure each temperature zone of said plurality of temperature zones, to change the number of the plurality of containers that can be stored in the respective temperature zone.

8. The system as recited in claim 1, wherein each temperature zone of the plurality of temperature zones is structured and arranged to store at least one of a container, multiple containers, a group of containers in a carrier, and a tray of containers.

9. The system as recited in claim 1, wherein each of the plurality of temperature zones includes at least one tray bin portion and corresponding removable tray portion that is adapted to be inserted into and removed from the at least one tray bin portion.

10. The system as recited in claim 9, wherein the removable tray portion includes a sealable upper compartment and a lower compartment that is at least one of selectively sealable and open.

11. The system as recited in claim 9, wherein the tray bin portions are structured and arranged in a multi-level carousel, each level providing space for at least one removable tray portion.

12. The system as recited in claim 1, wherein at least one of the front end portion, the rear end portion, and any of the tray portions includes at least one of an air register and an air vent configured to control a rate of flow of the warming or cooling fluid into a lower compartment of the tray portion.

13. The system as recited in claim 12, wherein the air register is manually or automatically controllable to selectively increase or selectively decrease the rate of fluid flow.

14. The system as recited in claim 1, wherein each of the temperature zones comprises a tray bin portion that is structured and arranged to receive and retain a removable tray portion that is adapted to hold at least one container, multiple containers or a group of containers.

15. The system as recited in claim 14, wherein the removable tray portion includes a sealable upper compartment and at least one of an open lower compartment and a partially open lower compartment.

16. The system as recited in claim 15, wherein the removable tray portion and the tray bin portion are structured and arranged so that when the removable tray portion is fully inserted into and properly seated within the tray bin portion a solid tray face portion on the tray portion produces a seal or barrier with a peripheral portion of a front opening of the tray bin portion, to prevent or minimize fluid flow into or out of the sealable upper compartment.

17. The system as recited in claim 15, wherein the lower compartment is structured and arranged to enable the cooling or warming fluid at the controlled temperature to circulate around any of the at least one containers disposed in the removable tray portion.

18. The system as recited in claim 15, wherein the fixed or removable tray bin portion includes a sealing door that is structured and arranged to produce a seal or barrier against the sealable upper compartment, to prevent or minimize fluid flow into or out of the upper compartment.

19. The system as recited in claim 15, wherein the source is structured and arranged to force the cooling or warming fluid at the controlled temperature into or through the lower compartment.

20. The system as recited in claim 1, wherein the at least one area having the plurality of temperature zones includes at least one multi-level shelf that is structured and arranged in an array of tray bins arranged in a plurality of horizontal rows and a plurality of vertical columns, and at least one temperature zone comprising at least a first tray bin and a second tray bin from one of an adjacent row and an adjacent column forming a tray bin portion.

21. The system as recited in claim 20, the system further comprising:
 a pair of multi-level shelves that are disposed opposite one another with access openings in the first multi-level shelf of the pair facing access openings in the second multi-level shelf of the pair; and
 a loading device disposed between a first shelf and a second shelf configured to load tray portions into a tray bin portion in either the first or the second shelf.

22. The system as recited in claim 1, wherein the plurality of temperatures zones includes a plurality of multi-level shelves that are disposed in an arcuate arrangement.

23. The system as recited in claim 9, wherein the tray portion includes a removable tray cover.

24. The system as recited in claim 1, wherein the plurality of temperatures zones includes a plurality of multi-level shelves that are adapted to be displaced in a Ferris wheel path.

25. The system as recited in claim 1, wherein the plurality of temperatures zones includes a plurality of multi-level shelves, each shelf of which is arranged in an array of vertical columns and horizontal rows and each multi-level shelf is movable in a direction orthogonal or substantially orthogonal to the plane of the columns and rows with respect to an adjacent shelf.

26. The system as recited in claim 1, wherein the plurality of temperatures zones includes a plurality of multi-level shelves that are adapted to be displaced in a serpentine path.

27. The system as recited in claim 9, wherein the tray bin portion includes at least one face adjacent to the source, the face being open, closed or partially open.

28. The system as recited in claim 27, wherein the face includes at least one fluid vent opening or at least one fluid vent opening with an air register.

29. A specimen inventory management system for holding a plurality of containers containing a sample under test in at least one of a pre-analytical phase, an in-process phase, and a post-analytical phase of processing at a storage temperature appropriate for the sample under test and the phase of processing, the system comprising:
 a source configured to provide a cooling or warming fluid having a controlled temperature to selective locations;
 at least one area having a plurality of temperature zones, each zone of said plurality of temperature zones being structured and arranged to hold a discrete number of the plurality of containers at a desired controlled temperature and/or controlled humidity, wherein the source selectively provides the cooling or warming fluid to the plurality of temperature zones;
 a container receiving and removal area configured to receive each of the plurality of containers and to insert said each of the plurality of containers in one of the plurality of temperatures zones, and to remove said each of the plurality of containers from a respective temperature zone for disposal or for analysis;
 a temperature equilibration area adapted to enable containers to reach a temperature equilibrium commensurate with a temperature at a next destination; and
 a controller configured to identify storage location and storage temperature of each of the plurality of containers, wherein each of the plurality of temperature zones includes at least one tray bin portion and corresponding removable tray portion that is adapted to be inserted into and removed from the at least one tray bin portion, and wherein the tray bin portion includes a pair of tray slide rails and a tray top of the tray portion is structured and arranged so that the tray top of the tray portion is in registration with and forms a substantially airtight seal with the pair of tray slide rails.

* * * * *